US00RE46095E

(19) United States
(12) Reissued Patent
Hacker et al.

(10) Patent Number: US RE46,095 E
(45) **Date of Reissued Patent: *Aug. 9, 2016**

(54) HERBICIDAL COMPOSITIONS

(71) Applicant: BAYER CROPSCIENCE AG, Monheim (DE)

(72) Inventors: Erwin Hacker, Hochheim (DE); Martin Hess, Mainz (DE); Martin Jeffrey Hills, Idstein (DE); Georg Bonfig-Picard, Rodenbach (DE); Thomas Auler, Leichlingen (DE)

(73) Assignee: Bayer Intellectual Property GmbH, Monheim (DE)

( * ) Notice: This patent is subject to a terminal disclaimer.

(21) Appl. No.: 14/596,041

(22) Filed: Jan. 13, 2015

Related U.S. Patent Documents

Reissue of:
(64) Patent No.: 8,586,503
Issued: Nov. 19, 2013
Appl. No.: 12/388,682
Filed: Feb. 19, 2009

(30) Foreign Application Priority Data

Feb. 21, 2008 (EP) ..... 08003156

(51) Int. Cl.
*A01N 43/68* (2006.01)
*C07D 251/48* (2006.01)

(52) U.S. Cl.
CPC ..... *A01N 43/68* (2013.01)

(58) Field of Classification Search
CPC ..... A01N 43/68; A01N 41/10; A01N 43/40; A01N 43/56; A01N 47/38; A01N 2300/00; A01N 43/12; A01N 43/54; A01N 43/80; A01N 47/36
USPC ..... 504/116.1, 232; 544/208
See application file for complete search history.

(56) References Cited

U.S. PATENT DOCUMENTS 8,426,342 B2 * 4/2013 Kilian ..... A01N 43/68 455/208
2006/0014642 A1 * 1/2006 Hacker et al. ..... A01N 43/68 504/133
2006/0019829 A1 1/2006 Hacker et al.

FOREIGN PATENT DOCUMENTS

CA 2344394 3/2000
WO WO 97/31904 9/1997
WO WO 00/16627 3/2000
WO WO 2006/007947 1/2006

OTHER PUBLICATIONS

Mannschreck et al. J. of Chemical Education v.84(12), 2007, 2012-2018.*

* cited by examiner

*Primary Examiner* — Evelyn Huang
(74) *Attorney, Agent, or Firm* — McBee Moore Woodward Vanik IP, LLC

(57) ABSTRACT

Herbicide combinations comprising an effective amount of components (A) and (B), where
component (A) is/are one or more herbicides of the formula (I) or salts thereof, (I)

in which
$R^1$ is H or a group of the formula $CZ^1Z^2Z^3$, where $Z^1$, $Z^2$ and $Z^3$ are as defined in claim 1, $R^2$ and $R^3$ are each H, alkyl, haloalkyl, alkenyl, haloalkenyl, alkynyl, haloalkynyl having in each case up to 4 carbon atoms or acyl, $R^4$ is H, $(C_1\text{-}C_6)$-alkyl or $(C_1\text{-}C_6)$-alkoxy;
$R^5$, $R^6$, $R^7$ and $R^8$ are each H, $(C_1\text{-}C_4)$-alkyl, $(C_1\text{-}C_3)$-haloalkyl, halogen, $(C_1\text{-}C_3)$-alkoxy, $(C_1\text{-}C_3)$-haloalkoxy or cyano;
A is $CH_2$ or O or a direct bond, and
the component (B) is one or more herbicides from the group of compounds consisting of
(B1) thiencarbazone, tembotrione, SYN-523, pyroxsulam, penoxsulam, SYN-449,
(B2) pyrasulfotole, trifloxysulfuron, saflufenacil, aminopyralid, ethofumesate, aminocyclopyrachlor and
(B3) pyroxasulfone (KIH-485)
are suitable for controlling harmful plants or for regulating the growth of plants.

16 Claims, No Drawings

HERBICIDAL COMPOSITIONS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*More than one reissue application has been filed for the reissue of U.S. Pat. No. 8,586,503. The reissue applications are application Ser. Nos. 14/596,041 (the present application) and 15/084,041, which is a reissue continuation of U.S. Pat. No. 8,586,503.*

The invention is in the technical field of crop protection products which can be used against unwanted vegetation on non-crop land, for preparing seed or in plant crops and which comprise, as herbicidally active compounds, a combination of at least two herbicides, where one herbicide component is selected from the group consisting of certain bicyclically substituted azines.

Compounds from the structural class of N-substituted diamino-s-triazines having bicyclic radicals on one amino group are known as herbicides (see, for example, WO-A-97/31904 or U.S. Pat. No. 6,069,114). The compounds are effective against a broad spectrum of harmful plants both when applied by the pre-emergence method and when applied by the post-emergence method, a non-selective use for controlling unwanted vegetation or a selective use in plant crops, if appropriate in combination with safeners, being possible.

The efficacy of these herbicides against harmful plants is at a high level, but depends in general on the application rate, the formulation in question, the spectrum of harmful plants, the harmful plants to be controlled in each case, the climatic and soil conditions and the like. Another criterion is the duration of action, or the breakdown rate of the herbicide. If appropriate, changes in the sensitivity of harmful plants, which may occur upon prolonged use of the herbicides or within geographic limitations, must also be taken into consideration. The compensation of losses in action in the case of individual harmful plants by increasing the application rates of the herbicides is only possible to a certain degree, for example because such a procedure frequently reduces the selectivity of the herbicides or because the action is not improved, even when applying higher rates. In some cases, the selectivity in crops can be improved by adding safeners. In general, however, there remains a need for methods to achieve the herbicidal action with a lower application rate of active compounds. Not only does a lower application rate reduce the amount of an active compound required for application, but, as a rule, it also reduces the amount of formulation auxiliaries required. It both reduces the economic input and improves the ecological compatibility of the herbicide treatment.

One possibility of improving the application profile of a herbicide can consist in combining the active compound with one or more other active compounds which contribute the desired additional properties. However, the combined use of a plurality of active compounds frequently causes phenomena of physical and biological incompatibility, for example a lack of stability in a coformulation, decomposition of an active compound, or antagonism of the active compounds. What is desired are, in contrast, combinations of active compounds having an advantageous activity profile, high stability and, if possible, an unexpected synergistically improved action, which allows the application rate to be reduced in comparison with the individual application of the active compounds to be combined.

It is already known that the combination of other herbicides with herbicides from the broadly defined class of the diamino-s-triazines which are N-substituted by arylalkyl radicals may result in synergistic effects (see WO-A-00/16627). Specific examples of combinations of other herbicides with diamino-s-triazines having bicyclic radicals on one amino group are not described in this publication. Owing to the relatively strong differences between the diamino-s-triazines having arylalkyl radicals on the amino group on the one hand and having bicyclic radicals on the other hand, where, in addition to the structural changes, differences can also be observed in changed activity characteristics, synergistic effects for the bicyclically substituted compounds, in particular individual stereoisomers thereof, are in principle not to be expected in the same manner.

WO 2006/007947 discloses herbicide combinations comprising, as common component, herbicides of the type of the 2,4-diamino-1,3,5-triazines substituted by bicyclic radicals at one of the amino groups. The herbicide combinations are suitable for controlling or combating unwanted vegetation in selective applications, for example in plantation crops, or in non-selective applications.

It was an object of the present invention to provide alternative or advantageous herbicide combinations having a good biological application profile and, ideally, a plurality of the desired favorable properties mentioned above.

The invention provides herbicide combinations comprising an effective amount of components (A) and (B) where component (A) is one or more herbicidally active compounds of the formula (I) or salts thereof [herbicides (A)]

(I)

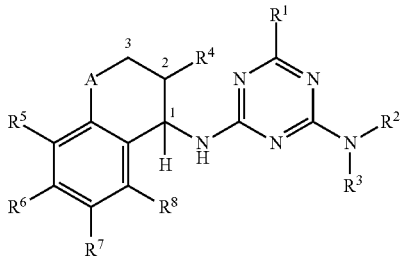

in which $R^1$ is H or a group of the formula $CZ^1Z^2Z^3$, where $Z^1$ is H, halogen, $(C_1-C_6)$-alkyl, $(C_1-C_6)$-haloalkyl, $[(C_1-C_4)$-alkoxy$]$-$(C_1-C_6)$-alkyl, $(C_3-C_6)$-cycloalkyl which is unsubstituted or substituted by one or more radicals selected from the group consisting of halogen, $(C_1-C_4)$-alkyl and $(C_1-C_4)$-haloalkyl, or is $(C_2-C_6)$-alkenyl, $(C_2-C_6)$-alkynyl, $(C_2-C_6)$-haloalkenyl, $(C_4-C_6)$-cyclo-alkenyl, $(C_4-C_6)$-halocycloalkenyl, $(C_1-C_6)$-alkoxy or $(C_1-C_6)$-halo-alkoxy, $Z^2$ is H, halogen, $(C_1-C_6)$-alkyl or $(C_1-C_4)$-alkoxy; or $Z^1$ and $Z^2$ together with the (shown) carbon atom of the group $CZ^1Z^2Z^3$ are a $(C_3-C_6)$-cycloalkyl radical or $(C_4-C_6)$-cycloalkenyl radical, where each of the two last-mentioned radicals is unsubstituted or substituted by one or more radicals selected from the group consisting of $(C_1-C_4)$-alkyl, and $Z^3$ is H, $(C_1-C_6)$-alkyl, $(C_1-C_4)$-alkoxy or halogen, $R^2$ and $R^3$ are each independently of one another H, ($C_1$-$C_4$)-alkyl, ($C_1$-$C_4$)-haloalkyl, ($C_3$-$C_4$)-alkenyl, ($C_3$-$C_4$)-haloalkenyl, ($C_3$-$C_4$)-alkynyl, ($C_3$-$C_4$)-haloalkynyl or an acyl radical.

$R^4$ is H, ($C_1$-$C_6$)-alkyl or ($C_1$-$C_6$)-alkoxy, $R^5$, $R^6$, $R^7$ and $R^8$ are each independently of one another H, ($C_1$-$C_4$)-alkyl, ($C_1$-$C_3$)-haloalkyl, halogen, ($C_1$-$C_3$)-alkoxy, ($C_1$-$C_3$)-haloalkoxy or cyano and A is a divalent group of the formula $CH_2$ or O or a direct bond, and component (B) is one or more herbicidally active compounds (B) selected from the group consisting of the herbicidally active compounds (B1), (B2) and (B3), where the herbicidally active compounds are (B1) herbicidally active compounds particularly suitable for post-emergence application against monocotyledonous or dicotyledonous harmful plants, selected from the group consisting of (B1.1) thiencarbazone and its esters and salts, (B1.2) tembotrione and its salts, (B1.3) ethyl [[3-[2-chloro-5-[3,6-dihydro-3-methyl-2,6-dioxo-4-(trifluoromethyl)-1(2H)-pyrimidinyl]-4-fluorophenoxy]-2-pyridinyl]oxy]acetate (SYN-523), (B1.4) pyroxsulam and its salts, (B1.5) penoxsulam and its salts, (B1.6) 4-hydroxy-3-[[2-[(2-methoxyethoxy)methyl]-6-trifluoromethyl-3-pyridinyl]carbonyl]bicyclo[3.2.1]oct-3-en-2-one (SYN-449) and its salts, (B2) herbicidally active compounds particularly suitable for post-emergence application against dicotyledonous harmful plants, selected from the group consisting of (B2.1) pyrasulfotole and its salts, (B2.2) trifloxysulfuron and its salts, (B2.3) saflufenacil and its salts, (B2.4) aminopyralid and its salts, (B2.5) ethofumesate, (B2.6) aminocyclopyrachlor and its salts and esters and (B3) herbicidally active compounds particularly suitable for pre-emergence application against monocotyledonous or dicotyledonous harmful plants, selected from the group consisting of (B3.1) pyroxasulfone (KIH-485).

The herbicide combinations according to the invention may comprise further components, for example other active compounds against harmful organisms such as harmful plants, plant-damaging animals or plant-damaging fungi, in particular active compounds selected from the group consisting of the herbicides, fungicides, insecticides, acaricides, nematicides and miticides and related substances, or else crop protection agents of a different type (for example safeners, resistance inductors), plant growth regulators and/or formulation auxiliaries and/or additives customary in crop protection. Here, the components may be formulated (finished formulation) and applied together, or they can be formulated separately and applied together, for example by the tank mix method or in a sequential application.

The individual herbicidally active compounds of the formula (I) present as component (A) are hereinbelow also referred to as compounds (A), active compounds (A) or herbicides (A). Correspondingly, the individual herbicidally active compounds present as component (B) are hereinbelow also referred to as compounds (B), active compounds (B) or herbicides (B).

An advantageous property found for the combination according to the invention of herbicides (A) and (B) is that the active compounds (A) and (B) are compatible with one another, i.e. they can be used together without substantial chemical incompatibilities of the active compounds (A) and/or (B) resulting in a decomposition of one or more active compounds. A reduction of the active compound content in formulations or spray liquors is thus avoided. The favorable compatibility also extends to the biological properties of the active compounds when applied in combination. Thus, antagonistic effects in the control of harmful plants are generally not observed with the active compound combinations according to the invention.

Accordingly, the active compounds (A) and (B) are particularly suitable for joint application or application additionally with further active crop protection agents or agrochemicals. The possible combined application allows advantageous effects to be utilized, such as, for example, the widening of the spectrum of the harmful plants to be controlled or to be combated in an application, a reduction of the application rate of the individual herbicides (A) and/or (B) compared to the respective application rate of the herbicide in question in an individual application. Thus, the degradation properties of the active compounds can be influenced, and more favorable conditions for the replanting of crop plants can be achieved. A further advantage consists in the fact that the development of resistances of harmful plants to the active compounds can frequently be reduced substantially or avoided by combinations of active compounds having a different mechanism of action.

In particular, surprisingly, there are also superadditive (=synergistic) effects in the combined application of the active compounds (A) and (B) with a relatively large number of economically important harmful plants. Here, the activity of the combination is stronger than the expected sum of the activities of the individual herbicides employed.

The synergistic effects allow the application rate to be reduced further, a broader spectrum of broad-leaved weeds and weed grasses to be controlled, a more rapid onset of the herbicidal action, a longer persistency, a better control of the harmful plants with only one or a few applications and a widening of the application period possible. To some extent, by using the compositions, the amount of harmful ingredients, such as nitrogen or oleic acid, and their introduction into the soil are also likewise reduced.

The abovementioned properties and advantages are desired for weed control practice to keep agricultural crops free of unwanted competing plants, and thus to ensure and/or increase yield levels from the qualitative and quantitative angle. These novel combinations markedly exceed the technical state of the art with a view to the properties described.

The synergistic effects are observed when the active compounds (A) and (B) are applied together; however, they may frequently also occur when the compounds are applied as a split application over time. Another possibility is the application of the herbicides (A) or (B) or the herbicide combinations (A) and (B) in a plurality of portions (sequential application). For example, one or more pre-emergence applications may be followed by a post-emergence application, or an early post-emergence application may be followed by applications at medium or late post-emergence. Preferred is the simultaneous or nearly simultaneous application of the active compounds of the combination in question, if appropriate in a plurality of portions. However, it is also possible to apply the individual active compounds of a combination at different times, which may be advantageous in the individual case. It is also possible to integrate other crop protection agents, such as, for example, the other active compounds mentioned (other herbidices, fungicides, insecticides, acaricides, etc.) and/or various auxiliaries, adjuvants and/or fertilizer applications in the system of application.

Application by the pre-emergence or post-emergence method is, depending on the context in which the terms are used, to be understood as meaning the application of the active compounds before or after the point in time when the harmful plants become visible above the ground, respectively, or the application of the active compounds against the harmful plants before the emergence of the crop plants and after the emergence of the crop plants, respectively.

In formula (I) for compounds of the herbicidally active compounds (A) and in all subsequent formulae, the following definitions apply:

The formula (I) also includes all stereoisomers of the compounds whose specific stereochemical configuration is not expressly expressed by the formula, and mixtures thereof. Such compounds of the formula (I) contain one or more asymmetrical carbon atoms or else double bonds which are not specifically shown in the general formulae (I). The formula (I) embraces all possible stereoisomers defined by their specific spatial form, such as enantiomers, diastereoisomers, Z and E isomers, and these stereoisomers can be obtained by customary methods from mixtures of the stereoisomers or else by stereoselective reactions in combination with the use of stereochemically pure starting materials.

By forming an adduct of a suitable inorganic or organic acid, such as, for example, HCl, HBr, $H_2SO_4$ or $HNO_3$, or else oxalic acid or sulfonic acids, to a basic group, such as, for example, amino or alkylamino, the compounds of the formula (I) are capable of forming salts, for example hydrochlorides, hydrobromides, hydrosulfates and hydrohydrogen sulfates. Suitable substituents present in deprotonated form, such as, for example, sulfonic acids or carboxylic acids, can form inner salts with groups which for their part are protonatable, such as amino groups. It is also possible to form salts by replacing the hydrogen of suitable substituents, such as, for example, sulfonic acids or carboxylic acids, by an agriculturally useful cation. These salts are, for example, metal salts, in particular alkali metal salts or alkaline earth metal salts, especially sodium and potassium salts, or else ammonium salts, salts with organic amines or quatemary ammonium salts.

The term "($C_1$-$C_4$)-alkyl" is an abbreviated notation for open-chain alkyl having one to 4 carbon atoms, i.e. it comprises the radicals methyl, ethyl, 1-propyl, 2-propyl, 1-butyl, 2-butyl, 2-methylpropyl or tert-butyl. Correspondingly, general alkyl radicals having a wider stated range of carbon atoms, for example "($C_1$-$C_6$)-alkyl", also comprise straight-chain or branched alkyl radicals having a larger number of carbon atoms, i.e., for example, also the alkyl radicals having 5 and 6 carbon atoms.

Unless specifically indicated, the lower carbon skeletons, for example those having 1 to 6 carbon atoms or, in the case of unsaturated groups, having 2 to 6 carbon atoms, are preferred for the hydrocarbon radicals, such as alkyl, alkenyl and alkynyl radicals, including in composite radicals. Alkyl radicals, including the composite meanings, such as alkoxy, haloalkyl, etc., are, for example, methyl, ethyl, n- or i-propyl, n-, i-, t- or 2-butyl, pentyls, hexyls, such as n-hexyl, i-hexyl and 1,3-dimethylbutyl, Heptyls, such as n-heptyl, 1-methylhexyl and 1,4-dimethylpentyl; alkenyl and alkynyl radicals denote the possible unsaturated radicals which correspond to the meaning of the alkyl radicals; alkenyl is, for example, vinyl, allyl, 1-methyl-2-propenyl, 2-methyl-2-propenyl, 2-butenyl, pentenyl, 2-methylpentenyl or hexenyl, preferably allyl, 1-methylprop-2-en-1-yl, 2-methyl-prop-2-en-1-yl, but-2-en-1-yl, but-3-en-1-yl, 1-methyl-but-3-en-1-yl or 1-methyl-but-2-en-1-yl. ($C_2$-$C_6$)-Alkynyl is, for example, ethynyl, propargyl, 1-methyl-2-propynyl, 2-methyl-2-propynyl, 2-butynyl, 2-pentynyl or 2-hexynyl, preferably propargyl, but-2-yn-1-yl, but-3-yn-1-yl or 1-methyl-but-3-yn-1-yl.

Cycloalkyl denotes a carbocyclic saturated ring system having preferably 3-8 carbon atoms, for example cyclopropyl, cyclobutyl, cyclopentyl or cyclohexyl.

Cycloalkenyl denotes a carbocyclic non-aromatic partially unsaturated ring system having preferably 4-8 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl.

Halogen denotes, for example, fluorine, chlorine, bromine or iodine. Haloalkyl, -alkenyl and -alkynyl denote alkyl, alkenyl and alkynyl, respectively, which are partially or fully substituted by identical or different halogen atoms, preferably selected from the group consisting of fluorine, chlorine and bromine, in particular from the group consisting of fluorine and chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

In the case of radicals having carbon atoms, preference is given to those having 1 to 4 carbon atoms, preferably 1 or 2 carbon atoms. Preference is generally given to substituents from the group consisting of halogen, for example fluorine and chlorine, ($C_1$-$C_4$)-alkyl, preferably methyl or ethyl, ($C_1$-$C_4$)-haloalkyl, preferably trifluoromethyl, ($C_1$-$C_4$)-alkoxy, preferably methoxy or ethoxy, ($C_1$-$C_4$)-haloalkoxy, nitro and cyano. Particular preference is given here to the substituents methyl, methoxy, fluorine and chlorine.

Acyl denotes a radical of an organic acid which, formally, is formed by removing a hydroxyl group from the acid function, it also being possible for the organic radical in the acid to be attached to the acid function via a heteroatom. Examples of acyl are the radical —CO—R of a carboxylic acid HO—CO—R and radicals of acids derived therefrom, such as thiocarboxylic acid, unsubstituted or N-substituted iminocarboxylic acids or the radical of carbonic acid monoesters, N-substituted carbamic acid, sulfonic acids, sulfinic acids, N-substituted sulfonamido acids, phosphonic acids, phosphinic acids.

Acyl denotes, for example, formyl, alkylcarbonyl, such as [($C_1$-$C_4$)-alkyl]-carbonyl, phenylcarbonyl, alkyloxycarbonyl, phenyloxycarbonyl, benzyloxycarbonyl, alkylsulfonyl, alkylsulfinyl, N-alkyl-1-iminoalkyl and other radicals of organic acids. Here, the radicals may in each case be substituted further in the alkyl or phenyl moiety, for example in the alkyl moiety by one or more radicals selected from the group consisting of halogen, alkoxy, phenyl and phenoxy; examples of substituents in the phenyl moiety are the substituents which have already been mentioned further above in a general manner for substituted phenyl.

Acyl preferably denotes an acyl radical in the narrower sense, i.e. a radical of an organic acid where the acid group is attached directly to the carbon atom of an organic radical, for example formyl, alkylcarbonyl, such as acetyl or [($C_1$-$C_4$)-alkyl]carbonyl, phenylcarbonyl, alkylsulfonyl, alkylsulfinyl and other radicals of organic acids.

If a general radical is designated (defined) as "hydrogen", this means an attached hydrogen atom.

The "yl-position" of a radical (for example of an alkyl radical) denotes its point of attachment.

Hereinbelow, compounds of the formula (I) and salts thereof which can be used according to the invention are, in short, also referred to as "compounds (I) according to the invention".

The compounds of the formula (I) are known in principle from WO 97/31904 or can be prepared by the processes described therein. Of particular interest are compounds of the formula (I) or salts thereof in which $R^1$ is H or a group of the formula $CZ^1Z^2Z^3$ in which $Z^1$ is H, halogen, $(C_1-C_4)$-alkyl, $(C_1-C_4)$-haloalkyl, $[(C_1-C_4)$-alkoxy$]$-$(C_1-C_6)$-alkyl or $(C_3-C_6)$-cycloalkyl which is unsubstituted or substituted by one or more radicals selected from the group consisting of $(C_1-C_4)$-alkyl, or is $(C_2-C_4)$-alkenyl, $(C_2-C_4)$-alkynyl, $(C_1-C_4)$-alkoxy or $(C_1-C_4)$-haloalkoxy;

$Z^2$ is H, halogen, $(C_1-C_4)$-alkyl or $Z^1$ and $Z^2$ together with the carbon atom attached to the radicals are a $(C_3-C_6)$-cycloalkyl radical and $Z^3$ is H, $(C_1-C_4)$-alkyl, $(C_1-C_2)$-alkoxy or halogen, $R^2$ is H, $(C_1-C_4)$-alkyl, $(C_1-C_4)$-haloalkyl, $(C_3-C_4)$-alkenyl, $(C_3-C_4)$-haloalkenyl, $(C_3-C_4)$-alkynyl, $(C_3-C_4)$-haloalkynyl or an acyl radical having 1 to 12 carbon atoms, wherein an acyl radical preferably is a acyl radical selected from the group consisting of formyl, phenylcarbonyl, phenoxycarbonyl, where phenyl in the two last-mentioned radicals is unsubstituted or substituted by one or more radicals from the group consisting of halogen, $(C_1-C_2)$-alkyl, $(C_1-C_2)$-haloalkyl, $(C_1-C_2)$-alkoxy, $(C_1-C_2)$-haloalkoxy and nitro, and $(C_1-C_6)$-alkyl-carbonyl, $(C_1-C_6)$-alkoxy-carbonyl and $(C_1-C_6)$-alkyl-sulfonyl, $R^3$ is H, $(C_1-C_4)$-alkyl or $(C_1-C_4)$-haloalkyl, $R^4$ is H, $(C_1-C_3)$-alkyl or $(C_1-C_3)$-alkoxy, $R^5$, $R^6$, $R^7$ and $R^8$ are each independently of one another H, $(C_1-C_3)$-alkyl, halogen, $(C_1-C_3)$-alkoxy, and A is a divalent group of the formula $CH_2$ or O or a direct bond, preferably $CH_2$ or a direct bond, in particular a direct bond.

Preference is given to optically active compounds of the formula (I) and salts thereof in which the stereochemical configuration at the carbon atom marked 1 in formula (I) is the (R)-configuration with a stereochemical purity of 60 to 100% (R), preferably 70-100% (R), in particular 80 to 100% (R), in each case based on the content of stereoisomers having (R)- and (S)-configuration in this position. The configuration is assumed to have been determined using the Cahn/Ingold/Prelog system, the priority of the substituents in position 1 being as follows:

1. priority is given to substituted NH; 2. priority is given to the bond to the phenyl ring; 3. priority is given to the other carbon ring atom, 4. priority is given to the hydrogen atom.

Preference is furthermore given to optically active compounds of the formula (I) and salts thereof in which $R^1$ is a group of the formula $CZ^1Z^2Z^3$, where $CZ^1Z^2Z^3$ is defined as above, in particular to those compounds in which the stereochemical configuration at the carbon atom of the group $CZ^1Z^2Z^3$ is the (R,S)-configuration or the (R)-configuration with a stereochemical purity of 60 to 100% (R), preferably 70-100% (R), in particular 80 to 100% (R), in each case based on the content of stereoisomers having (R)- and (S)-configuration in this position.

Suitable combination partners (A) are, for example, certain compounds of the formula (I) from Table 1 below.

Notes for Table 1: In Table 1, the compounds are designated by the chemical formula of the main component, this component being present in a chemical purity of at least 95% by weight of the compound. It is, of course, also possible to use the compounds in lower purities. In particular if minor components of the compounds consist predominantly or entirely of active stereoisomers of the respective compounds (A), similar efficacies are achieved during application. Accordingly, preferred herbicides (A) are also mixtures of two or more compounds (A) from Table 1. For reasons of easier preparability, in practice, preference is especially also given to herbicides (A) comprising, as main component, a compound (A) from Table 1 and, as minor components, stereoisomers of the compound (A), preferably those which are also mentioned in Table 1.

If, in the chemical formula in question in Table 1, the stereochemical orientation at a carbon atom is given and the stereochemical orientation is additionally assigned using the system of Cahn, Ingold and Prelog, the main component of the compound is a stereoisomer or a stereoisomer mixture which has the R- or S-configuration at the carbon atom referred to; the compound (A) is thus optically active.

If the stereochemistry is not assigned by an R- or S-configuration, the main component is a compound which, at the carbon atom in question, has the RS-configuration (racemic).

If a plurality of stereocenters are present and the configuration is in each case assigned by R or S, these are optically active compounds having the stereochemistry mentioned at the centers referred to.

If, in the case of a plurality of centers, no R- or S-configuration is assigned, the compounds are racemic mixtures, i.e. the non-chiral stereoisomers contained therein (enantiomers of a pair of enantiomers) are present in the mixture in identical proportions. Unless indicated in more detail, in Table 1, in the case of racemic compounds (A) having a plurality of stereocenters, the diastereoisomeric components are present in approximately identical proportions. However, for practical application, in the case of racemic compounds having a plurality of stereocenters, mixtures of diastereomers (in each case in racemic form) having different proportions of the diastereomeric components are possible.

In the bicyclic radical, the carbon atom which is attached to the amino group is carbon atom 1. In the side group (unless the radical is H) the carbon atom attached directly to the triazine ring is referred to as 1*.

TABLE 1

Compounds of the formula (I) (herbicide (A)):

| Compound No. | Chemical formula or chemical name |
|---|---|
| A1 | 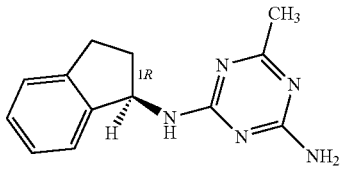 |
| A2 | 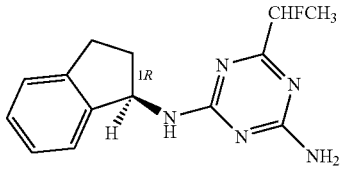 |

TABLE 1-continued
Compounds of the formula (I) (herbicide (A)):
| Compound No. | Chemical formula or chemical name |
|---|---|
| A3 | 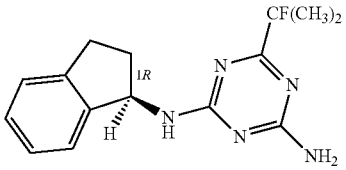 |
| A4 | 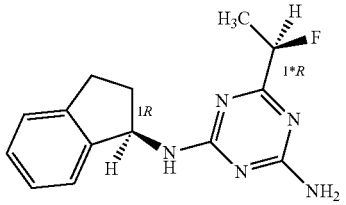 |
| A5 | 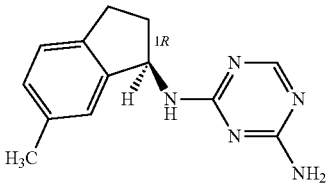 |
| A6 | 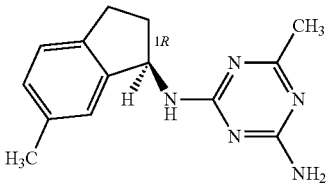 |
| A7 | 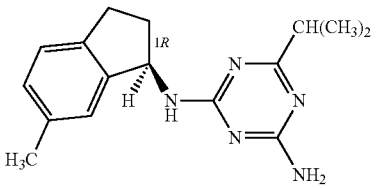 |
| A8 | 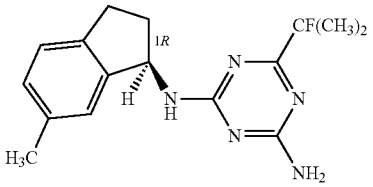 |
| A9 | 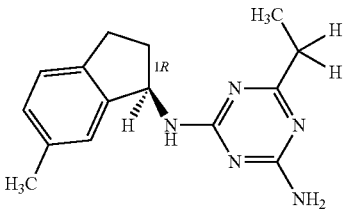 |
TABLE 1-continued
Compounds of the formula (I) (herbicide (A)):
| Compound No. | Chemical formula or chemical name |
|---|---|
| A10 | 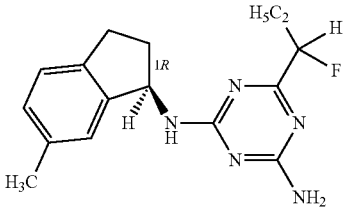 |
| A11 | 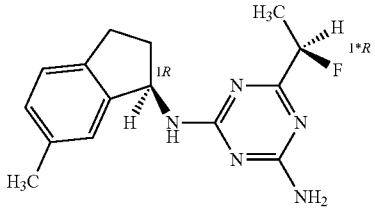 |
| A12 | 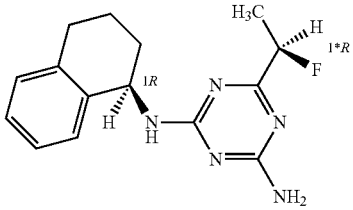 |
| A13 | 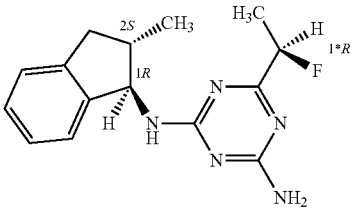 |
| A14 | 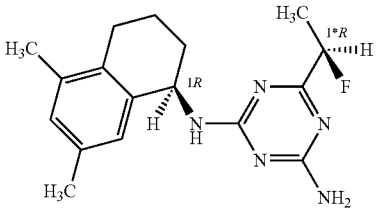 |
| A15 | 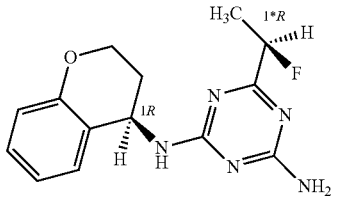 |
| A16 | 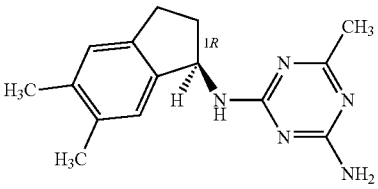 |

TABLE 1-continued
Compounds of the formula (I) (herbicide (A)):
| Compound No. | Chemical formula or chemical name |
|---|---|
| A17 | 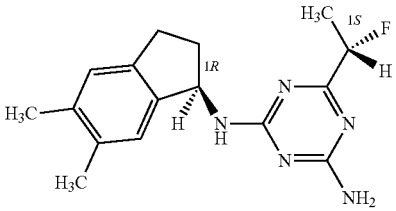 |
| A18 | 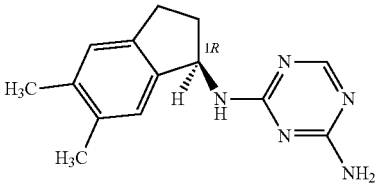 |
| A19 | 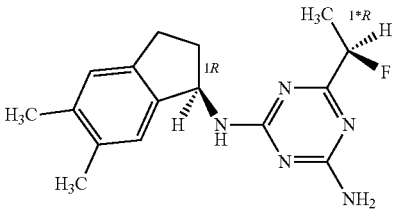 |
| A20 | 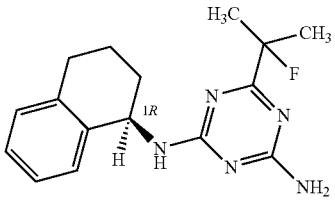 |
| A21 | 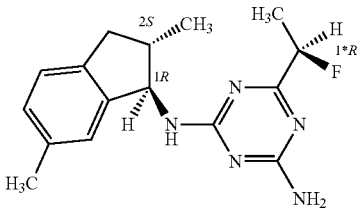 |
| A22 | 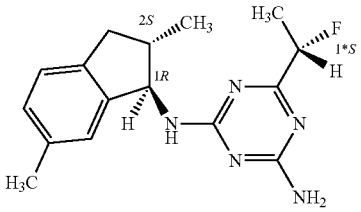 |
| A23 | 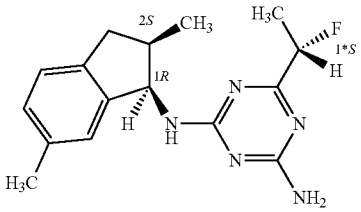 |
TABLE 1-continued
Compounds of the formula (I) (herbicide (A)):
| Compound No. | Chemical formula or chemical name |
|---|---|
| A24 | 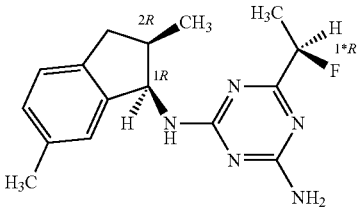 |
| A25 | 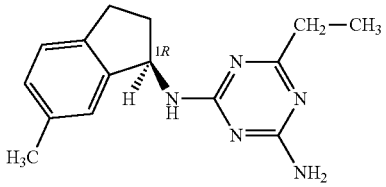 |
| A26 | 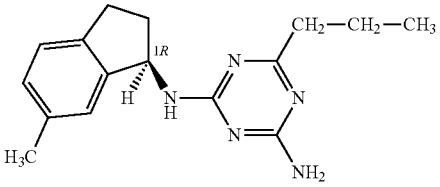 |
| A27 | 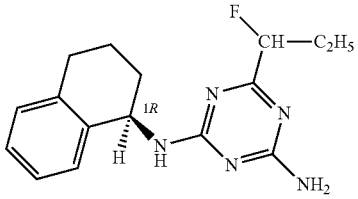 |
| A28 | 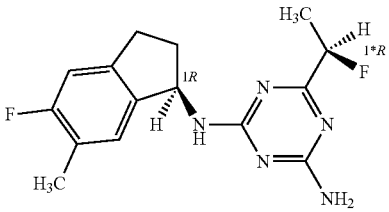 |
| A29 | 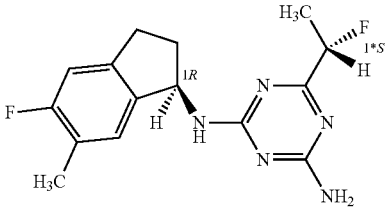 |

TABLE 1-continued
Compounds of the formula (I) (herbicide (A)):
| Compound No. | Chemical formula or chemical name |
|---|---|
| A30 | 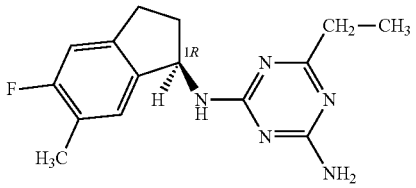 |
| A31 | 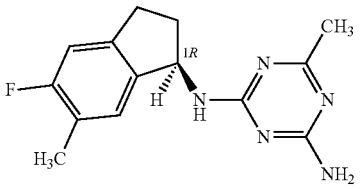 |
| A32 | 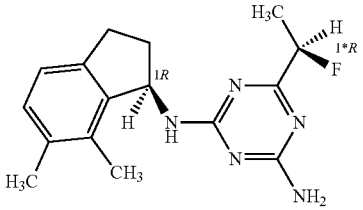 |
| A33 | 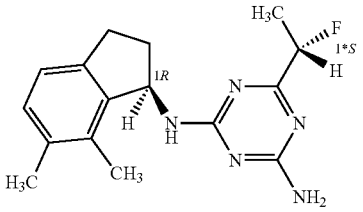 |
| A34 | 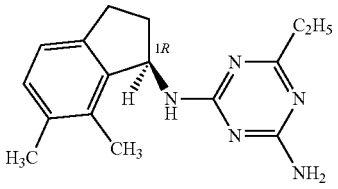 |
| A35 | 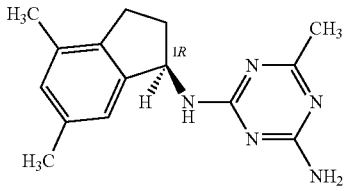 |
| A36 | 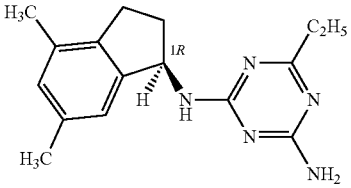 |
TABLE 1-continued
Compounds of the formula (I) (herbicide (A)):
| Compound No. | Chemical formula or chemical name |
|---|---|
| A37 | 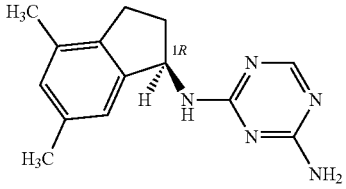 |
| A38 | 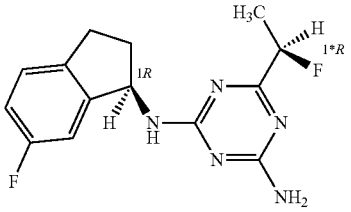 |
| A39 | 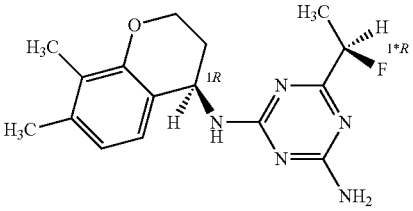 |
| A40 | 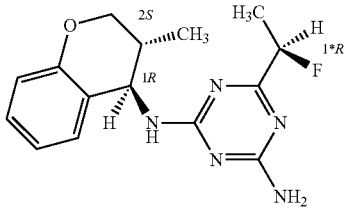 |
| A41 | 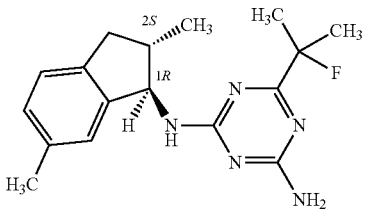 |
| A42 | 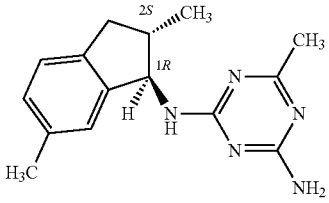 |

TABLE 1-continued
Compounds of the formula (I) (herbicide (A)):
| Compound No. | Chemical formula or chemical name |
|---|---|
| A43 | 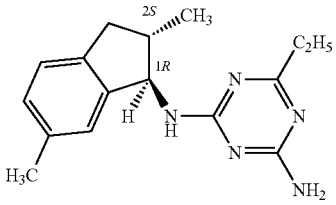 |
| A44 | 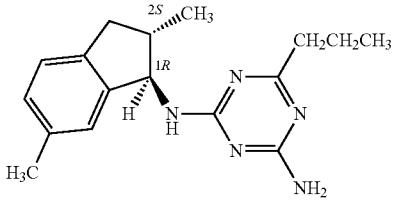 |
| A45 | 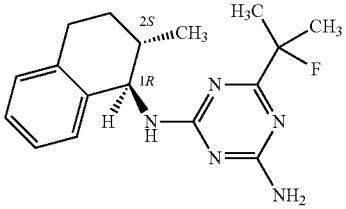 |
| A46 | 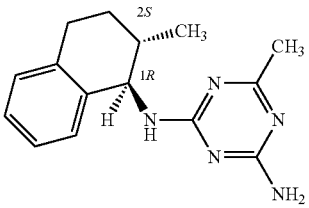 |
| A47 | 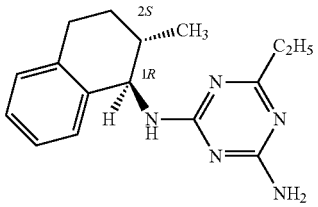 |
| A48 | 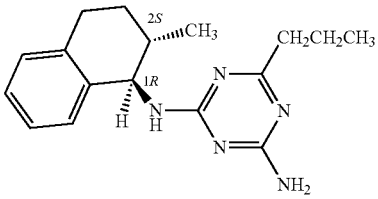 |
TABLE 1-continued
Compounds of the formula (I) (herbicide (A)):
| Compound No. | Chemical formula or chemical name |
|---|---|
| A49 | 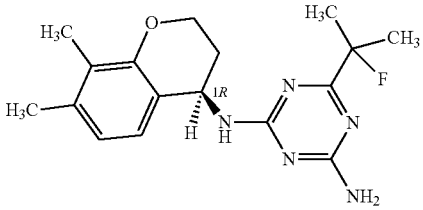 |
| A50 | 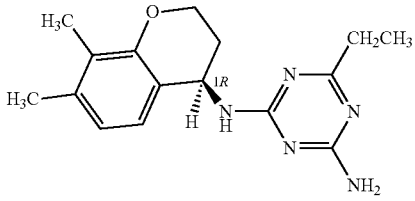 |
| A51 | 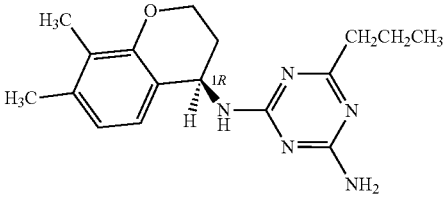 |
| A52 | 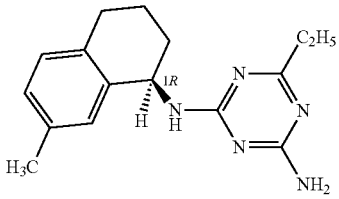 |
| A53 | 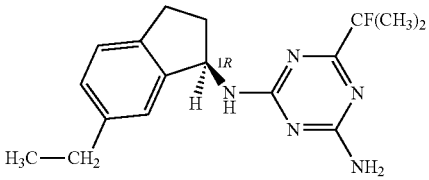 |
| A54 | 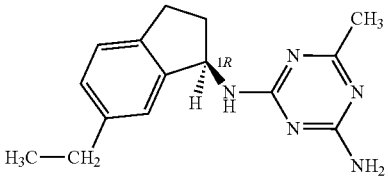 |
| A55 | 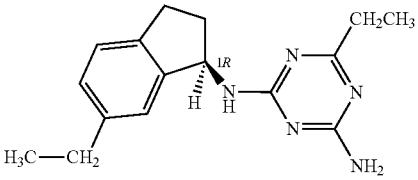 |

TABLE 1-continued
Compounds of the formula (I) (herbicide (A)):
| Compound No. | Chemical formula or chemical name |
|---|---|
| A56 | 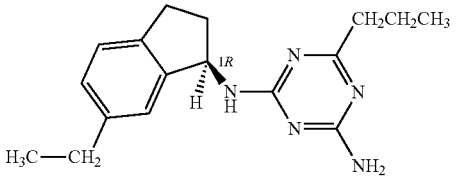 |
| A57 | 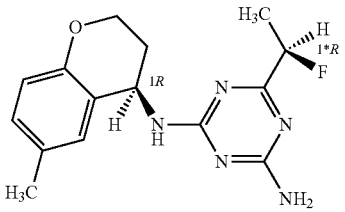 |
| A58 | 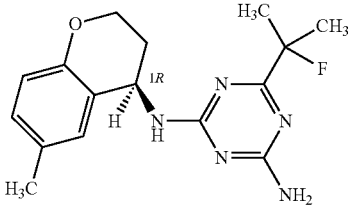 |
| A59 | 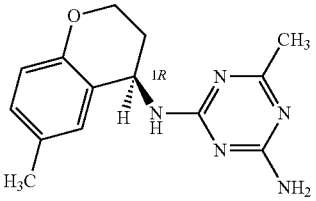 |
| A60 | 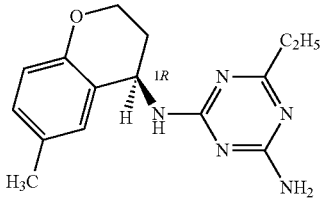 |
| A61 | 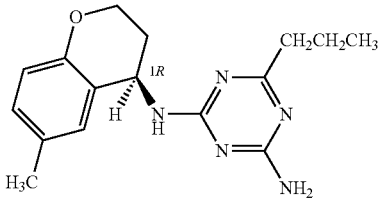 |
| A62 | 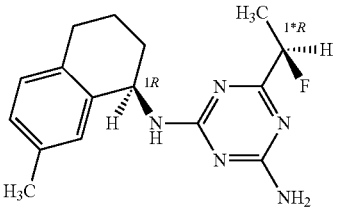 |
TABLE 1-continued
Compounds of the formula (I) (herbicide (A)):
| Compound No. | Chemical formula or chemical name |
|---|---|
| A63 | 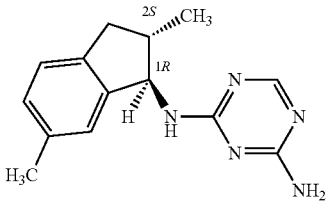 |
| A64 | 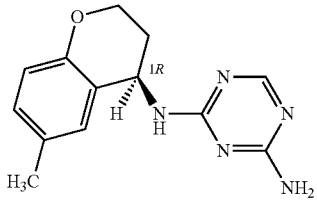 |
| A65 | 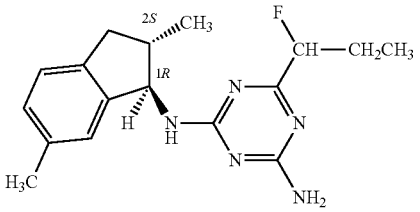 |
| A66 | 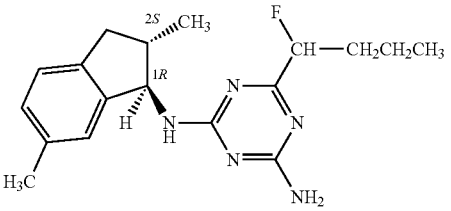 |
| A67 | 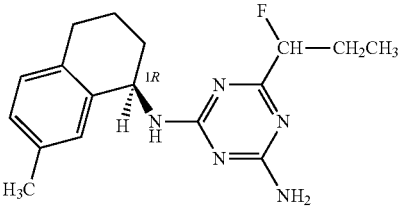 |
| A68 | 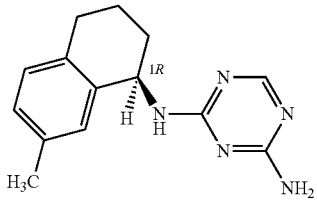 |
| A69 | 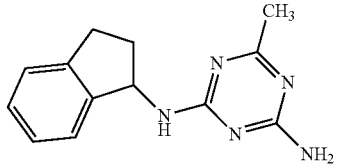 |

TABLE 1-continued
Compounds of the formula (I) (herbicide (A)):
| Compound No. | Chemical formula or chemical name |
|---|---|
| A70 | 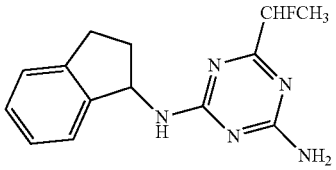 |
| A71 | 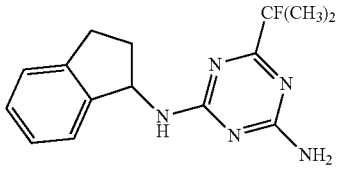 |
| A72 | 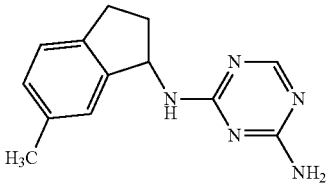 |
| A73 | 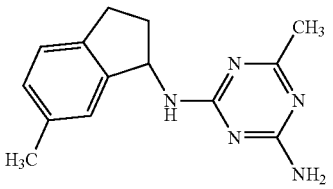 |
| A74 | 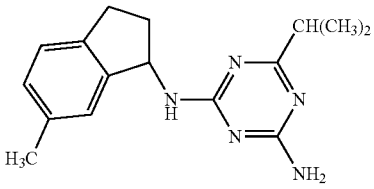 |
| A75 | 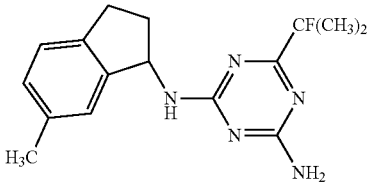 |
| A76 | 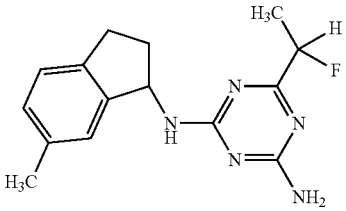 |
TABLE 1-continued
Compounds of the formula (I) (herbicide (A)):
| Compound No. | Chemical formula or chemical name |
|---|---|
| A77 | 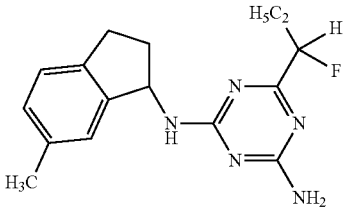 |
| A78 | 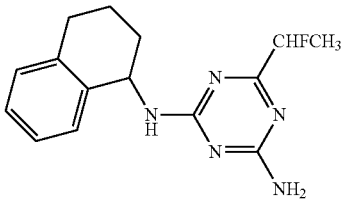 |
| A79 | 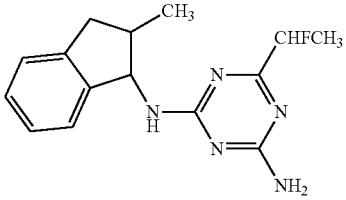 |
| A80 | 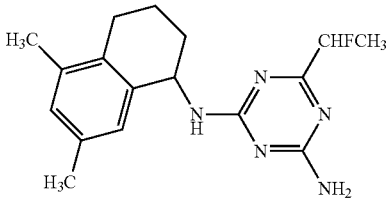 |
| A81 | 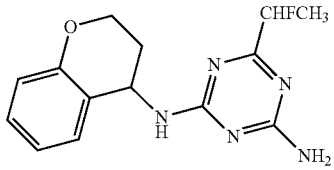 |
| A82 | 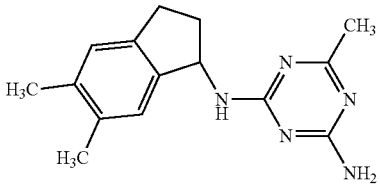 |
| A83 | 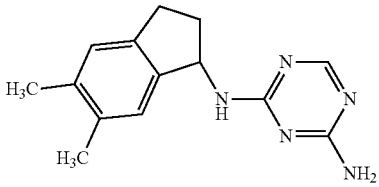 |

TABLE 1-continued
Compounds of the formula (I) (herbicide (A)):
| Compound No. | Chemical formula or chemical name |
|---|---|
| A84 | 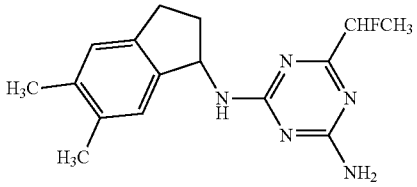 |
| A85 | 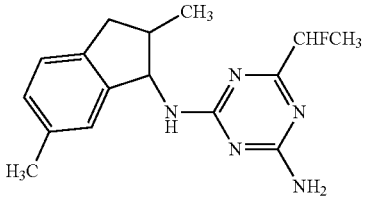 |
| A86 | 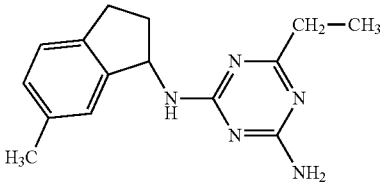 |
| A87 | 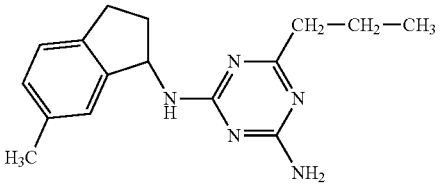 |
| A88 | 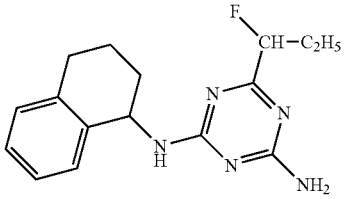 |
| A89 | 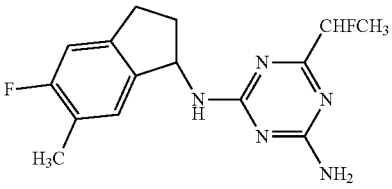 |
| A90 | 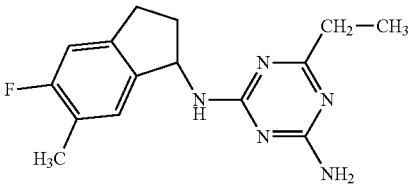 |
TABLE 1-continued
Compounds of the formula (I) (herbicide (A)):
| Compound No. | Chemical formula or chemical name |
|---|---|
| A91 | 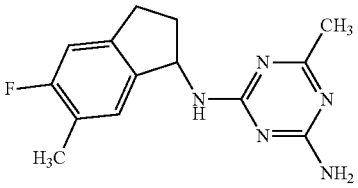 |
| A92 | 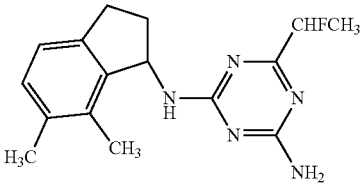 |
| A93 | 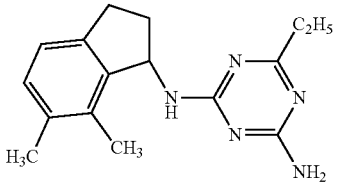 |
| A94 | 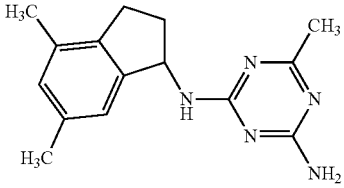 |
| A95 | 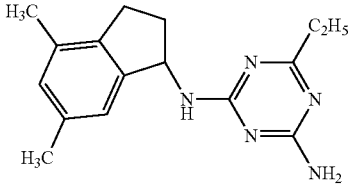 |
| A96 | 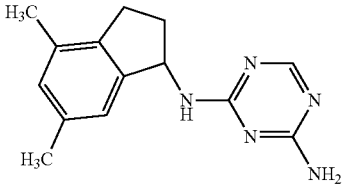 |
| A97 | 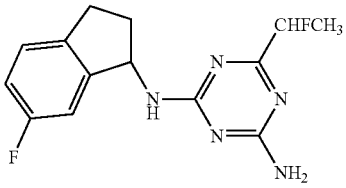 |

TABLE 1-continued
Compounds of the formula (I) (herbicide (A)):
| Compound No. | Chemical formula or chemical name |
|---|---|
| A98 | 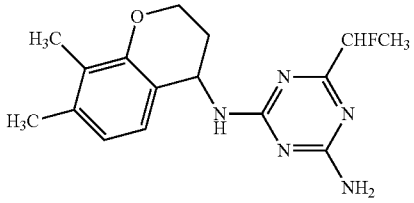 |
| A99 | 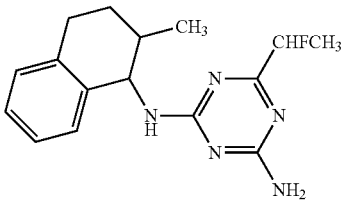 |
| A100 | 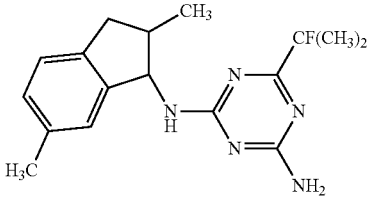 |
| A101 | 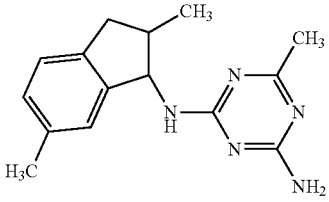 |
| A102 | 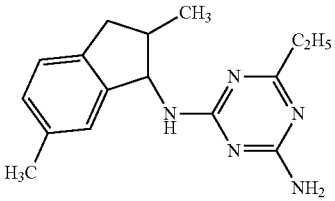 |
| A103 | 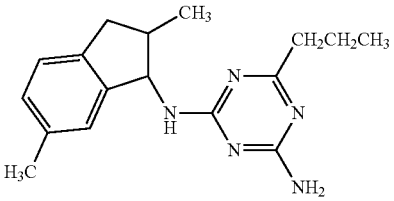 |
| A104 | 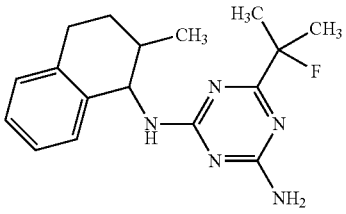 |
TABLE 1-continued
Compounds of the formula (I) (herbicide (A)):
| Compound No. | Chemical formula or chemical name |
|---|---|
| A105 | 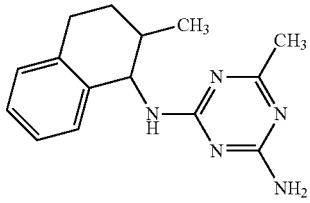 |
| A106 | 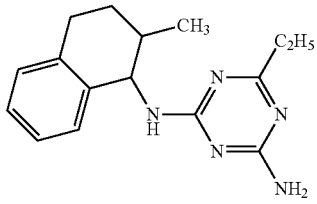 |
| A107 | 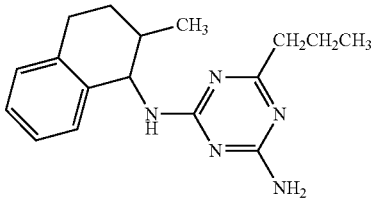 |
| A108 | 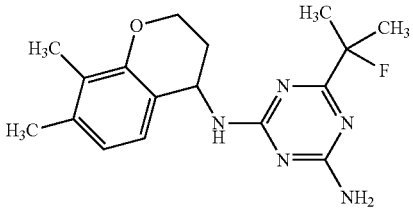 |
| A109 | 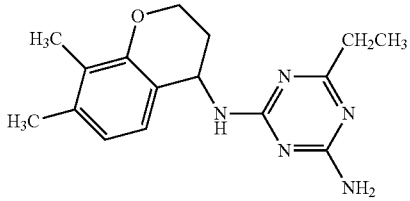 |
| A110 | 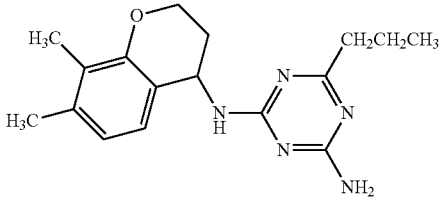 |
| A111 | 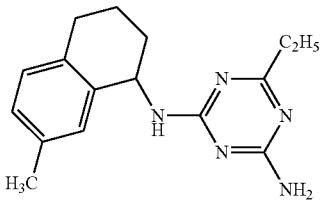 |

TABLE 1-continued
Compounds of the formula (I) (herbicide (A)):
| Compound No. | Chemical formula or chemical name |
|---|---|
| A112 | 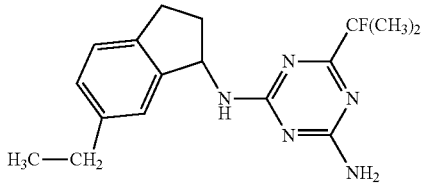 |
| A113 | 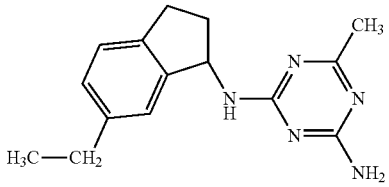 |
| A114 | 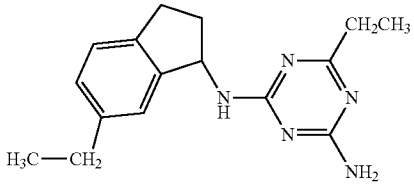 |
| A115 | 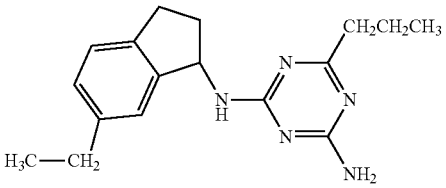 |
| A116 | 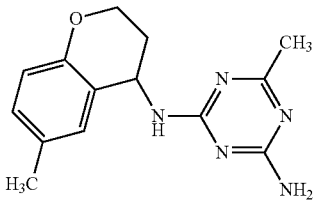 |
| A117 | 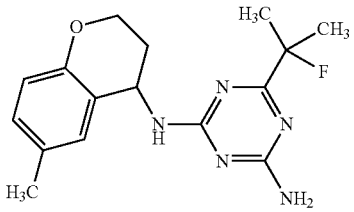 |
| A118 | 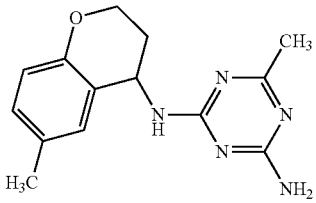 |
TABLE 1-continued
Compounds of the formula (I) (herbicide (A)):
| Compound No. | Chemical formula or chemical name |
|---|---|
| A119 | 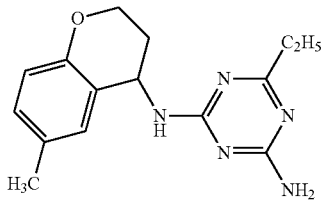 |
| A120 | 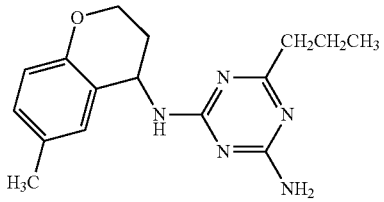 |
| A121 | 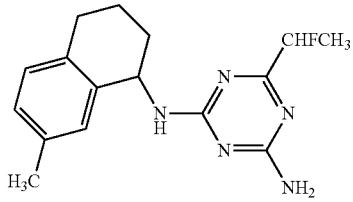 |
| A122 | 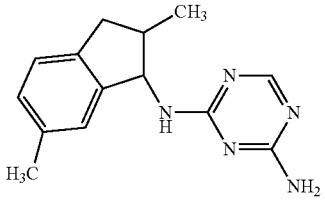 |
| A123 | 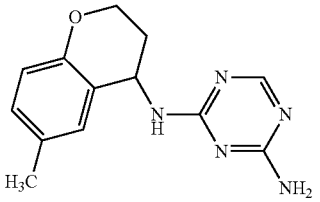 |
| A124 | 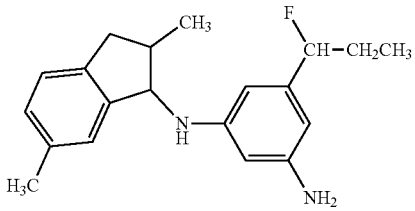 |
| A125 | 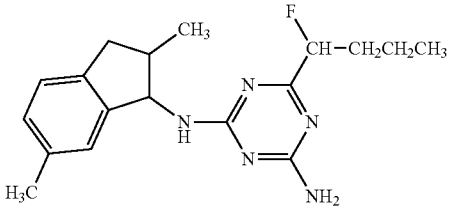 |

TABLE 1-continued

| Compounds of the formula (I) (herbicide (A)): | |
|---|---|
| Compound No. | Chemical formula or chemical name |
| A126 | 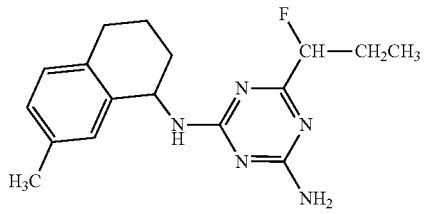 |
| A127 | 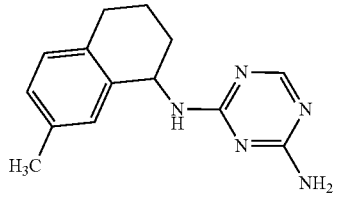 |

The application rates of the herbicides (A) are known in principle and are in the range from 0.01 to 2000 g of active compound per hectare, preferably from 0.02 to 1000 g of active compound per hectare, in particular from 0.5 to 750 g of active compound per hectare. In the combinations according to the invention, in the context of the application rates mentioned, mainly lower application rates of the active compound in question are required compared to the application on its own, preferably 0.01 to 1000 g of active substance per hectare, in particular 0.02 to 500 g of active substance per hectare.

Preferred combination partners (A) are the compounds of table 1 in which the 2,4-diamino-s-triazine moiety is N-substituted by an optionally substituted indanyl radical, tetrahydronaphthyl radical or 4-chromanyl radical. Preference is given here to the compounds (Al), (A2), (A3), (A4), (A5), (A6), (A7), (A8), (A9), (A10), (A11), (A13), (A16), (A17), (A18), (A19), (A21), (A22), (A23), (A24), (A25), (A26), (A28), (A29), (A30), (A31), (A32), (A33), (A34), (A35), (A36), (A37), (A38), (A41), (A42), (A43), (A44), (A53), (A54), (A55), (A56), (A63), (A65), (A66), (A69), (A70), (A71), (A72), (A73), (A74), (A75), (A76), (A77), (A79), (A82), (A83), (A84), (A85), (A86), (A87), (A89), (A90), (A91), (A92), (A93), (A94), (A95), (A96), (A97), (A100), (A101), (A102), (A103), (A112), (A113), (A114), (A115), (A122), (A124), (A125) and their mixtures.

Preference is here also given to the optically active compounds (A1), (A2), (A3), (A4), (A5), (A6), (A7), (A8), (A9), (A10), (A11), (A13), (A16), (A17), (A18), (A19), (A21), (A22), (A23), (A24), (A25), (A26), (A28), (A29), (A30), (A31), (A32), (A33), (A34), (A35), (A36), (A37), (A38), (41), (A42), (A43), (A44), (A53), (A54), (A55), (A56), (A63), (A65), (A66), (A69) listed in each case having a stereochemical purity (optical purity) with respect to the carbon atom in position 1 of from 60 to 100% (R), preferably 70-100% (R), in particular from 80 to 100% (R), in each case based on the content of stereoisomers having (R) and (S) configuration in this position. Preferred components (A) also include mixtures of the optically active compounds (A) mentioned above, preferably those having the same chemical constitution, which differ only in the stereochemical configuration. Preference is given, for example, to optically active mixtures of the compounds (A9)+(A11), (A21)+(A22), (A23)+(A24), (A28)+(A29), (A32)+(A33), where the ratios may be varied within a wide range.

Preference is also given to the racemic compounds (A69), (A70), (A71), (A72), (A73), (A74), (A75), (A76), (A77), (A79), (A82), (A83), (A84), (A85), (A86), (A87), (A89), (A90), (A91), (A92), (A93), (A94), (A95), (A96), (A97), (A100), (A101), (A102), (A103), (A112), (A113), (A114), (A115), (A122), (A124), (A125) listed and their mixtures.

Preference is also given to the compounds (A12), (A14), (A20), (A27), (A40), (A45), (A46), (A47), (A48), (A52), (A62), (A67), (A68), (A78), (A80), (A88), (A99), (A104), (A105), (A106), (A107), (A111), (A116), (A121), (A126), (A127) and their mixtures. With respect to the racemic compounds and the optical purities, what was said above applies correspondingly to this group of compounds.

Preference is also given to the compounds (A15), (A39), (A49), (A50), (A51), (A57), (A58), (A59), (A60), (A61), (A64), (A81), (A98), (A108), (A109), (A110), (A116), (A117), (A118), (A119), (A120), (A123) and their mixtures. With respect to the racemic compounds and the optical properties, what was said above for this group of compounds applies correspondingly.

Suitable combination partners (B) [=component (B)] are active compounds of subgroups (B1) to (B3), where the herbicidally active compounds are in most cases referred to by the "common name" according to the literature reference "The Pesticide Manual" 14th Ed., British Crop Protection Council 2006, abbreviated as "PM" or the chemical name according to the customary nomenclatures (IUPAC or Chemical Abstracts):

The herbicidally active compounds from the group consisting of (B1), (B2) and (B3) are individually as hereinbelow:

(B1) herbicidally active compounds which are particularly suitable for post-emergence application against monocotyledonous or dicotyledonous harmful plants, selected from the group consisting of (B1.1) thiencarbazone and its esters and salts (WO 01/05788), in particular (B1.1.1) thiencarbazone, i.e. the chemical compound 4-[(4,5-dihydro-3-methoxy-4-methyl-5-oxo-1H-1,2,4-triazol-1-yl)carbonyl-sulfamoyl]-5-methylthiophene-3-carboxylic acid of the formula:

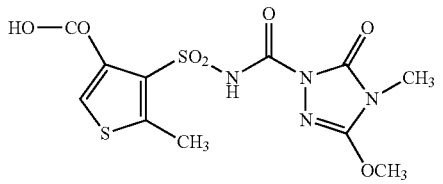

(B1.1.2) thiencarbazone-methyl, i.e. the chemical compound methyl 4-[(4,5-dihydro-3-methoxy-4-methyl-5-oxo-1H-1,2,4-triazol-1-yl)carbonylsulfamoyl]-5-methylthiophene-3-carboxylate [CAS-Reg. 317815-83-1] or (B1.1.3) thiencarbazone-methyl sodium salt, i.e. the compound methyl 4-[(4,5-dihydro-3-methoxy-4-methyl-5-oxo-1H-1,2,4-triazol-1-yl)carbonylsulfamoyl]-5-methylthiophene-3-carboxylate sodium, i.e. the acidic hydrogen atom at the sulfonamide group in thiencarbazone-methyl has been replaced by a sodium atom, (B1.2) tembotrione and its salts, for example its alkali metal salts, such as sodium or potassium salts (see WO-A-00/21924), in particular (B1.2.1) tembotrione, i.e. the chemical compound 2-{2-chloro-4-mesyl-3-[(2,2,2-trifluoroethoxy)methyl] benzoyl}cyclohexane-1,3-dione [CAS-Reg. 335104-84-2] of the formula (the formula only shows the triketo form, which is generally in an equilibrium with a plurality of possible enol forms):

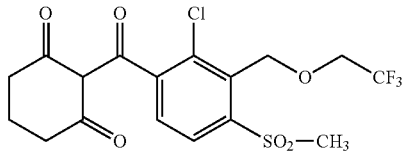

(B1.3) ethyl [[3-[2-chloro-5-[3,6-dihydro-3-methyl-2,6-dioxo-4-(trifluoromethyl)-1(2H)-pyrimidinyl]-4-fluorophenoxy]-2-pyridinyl]oxy]acetate (herein also referred to as SYN-523) (WO 2006/061562, EP 1122244) of the formula

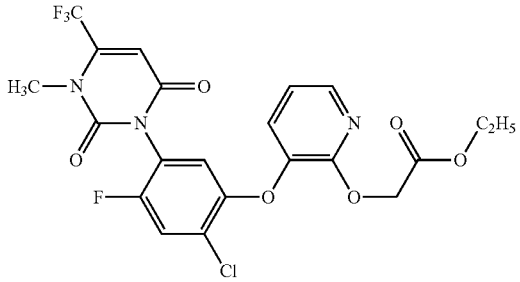

(B1.4) pyroxsulam and its salts, for example its alkali metal salts, such as sodium or potassium salts, in particular (B1.4.1) pyroxsulam, i.e. the chemical compound N-(5,7-dimethoxy[1,2,4]triazolo[1,5-a]pyrimidin-2-yl)-2-methoxy-4-(trifluoromethyl)pyridine-3-sulfonamide [CAS-Reg. 422556-08-9] of the formula:

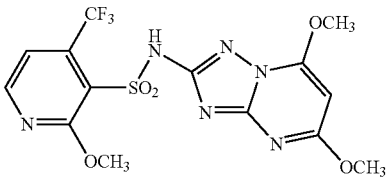

(B1.5) penoxsulam and its salts, for example its alkali metal salts, such as sodium or potassium salts, in particular (B1.5.1) penoxsulam, i.e. the chemical compound 2-(2,2-difluoroethoxy)-N-(5,8-dimethoxy[1,2,4]triazolo[1,5-c]pyrimidin-2-yl)-6-(trifluoromethyl)benzenesulfonamide [CAS-Reg. 219714-96-2] of the formula:

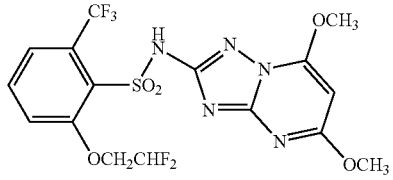

and (B1.6) 4-hydroxy-3-[[2-[(2-methoxyethoxy)methyl]-6-trifluoromethyl-3-pyridinyl]carbonyl]bicyclo[3.2.1]oct-3-en-2-one and its salts, for example its alkali metal salts, such as sodium or potassium salts, in particular (B1.6.1) SYN-449, i.e. the chemical compound 4-hydroxy-3-[[2-[(2-methoxyethoxy)methyl]-6-trifluoromethyl-3-pyridinyl]carbonyl]-bicyclo[3.2.1]oct-3-en-2-one (CAS RN 352010-68-5, SYN-449, WO-A-2006/097322, WO-A-01/94339) of the formula (the formula shows only one of the possible enol forms which are generally in an equilibrium with one another and with the keto form=the triketone):

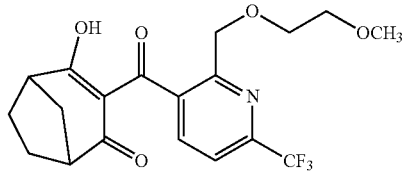

(B2) herbicidally active compounds which are particularly suitable for post-emergence application against dicotyledonous harmful plants, selected from the group consisting of (B2.1) pyrasulfotole and its salts, for example its alkali metal salts, such as sodium or potassium salts, in particular (B2.1.1) pyrasulfotole, i.e. the chemical compound (5-hydroxy-1,3-dimethyl-1H-pyrazol-4-yl)-[2-(methylsulfonyl)-4-(trifluoromethyl)-phenyl]methanone [CAS-Reg. 365400-11-9] of the formula:

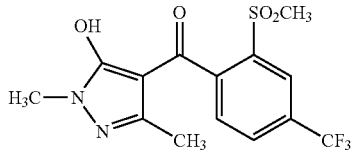

(B2.2) trifloxysulfuron and its salts, for example its alkali metal salts, such as sodium or potassium salts, in particular (B2.2.1) trifloxysulfuron, i.e. the chemical compound 1-(4,6-dimethoxypyrimidin-2-yl)-3-[3-(2,2,2-trifluoroethoxy)-2-pyridylsulfonyl]urea of the formula:

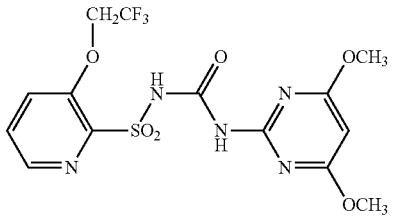

or, preferably.

(B2.2.2) trifloxysulfuron-sodium, i.e. the sodium salt of trifloxysulfuron in which the acidic hydrogen atom at the sulfonamide group has been replaced by a sodium atom;

(B2.3) saflufenacil and its salts, for example its alkali metal salts, such as sodium or potassium salts, in particular (B2.3.1) saflufenacil (herein also referred to as BAS-H800), i.e. the chemical compound 2-chloro-5-[3,6-dihydro-3-methyl-2,6-dioxo-4-(trifluoromethyl)-1(2H)-pyrimidinyl]-4-fluoro-N-[[methyl(1-methylethyl)amino]sulfonyl]benzamide [CAS-Reg. 372137-35-4] (WO 2001/083459) of the formula:

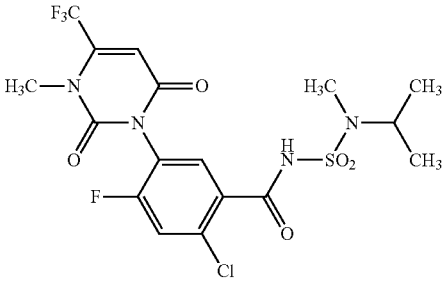

(B2.4) aminopyralid and its salts, for example its alkali metal salts, such as sodium or potassium salts, or ammonium salts or else acid addition salts (for example hydrochlorides), in particular (B2.4.1) aminopyralid, i.e. the chemical compound 4-amino-3,6-dichloropyridine-2-carboxylic acid [CAS-Reg. 150114-71-9] of the formula:

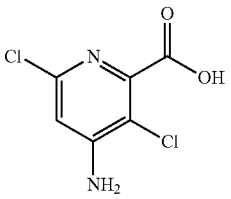

and (B2.5) ethofumesate, i.e. the chemical compound (RS)—O-(2-ethoxy-2,3-dihydro-3,3-dimethylbenzofuran-5-yl)methanesulfonate [CAS-Reg. 26225-79-6] of the formula:

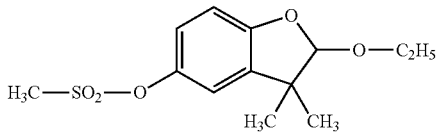

(B2.6) aminocyclopyrachlor and its salts and esters, for example its alkali metal salts, such as sodium or potassium salts, and its alkyl esters, such as ($C_1$-$C_4$)-alkyl ester, preferably (B2.6.1) aminocyclopyrachlor, i.e. the chemical compound 6-amino-5-chloro-2-cyclopropylpyrimidine-4-carboxylic acid [CAS-Reg. 858958-08-8] of the formula:

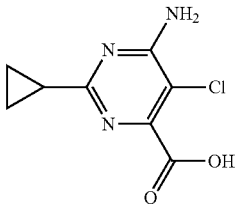

or preferably also (B2.6.2) aminocyclopyrachlor potassium salt or (B2.6.3) aminocyclopyrachlor sodium salt or (B2.6.4) aminocyclopyrachlor methyl ester and (B3) herbicidally active compounds which are particularly suitable for pre-emergence application against monocotyledonous or dicotyledonous harmful plants, selected from the group consisting of (B3.1) pyroxasulfone (KIH-485), i.e. the chemical compound 3-[5-(difluoromethoxy)-1-methyl-3-(trifluoromethyl)pyrazol-4-ylmethylsulfonyl]-4,5-dihydro-5,5-dimethyl-1,2-oxazole [CAS-Reg. 447399-55-5] of the formula:

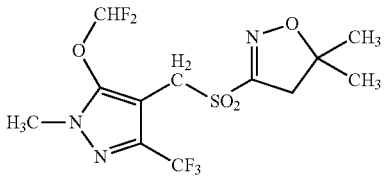

With respect to the target plants and the application period, the combination partners (B) used according to the invention are functionally similar, which is why they are classified in the same functional group of combination partners: however, in some cases they differ with respect to the class of chemical compound and the biological mechanism of action and thus generally in some cases also with respect to the application rate and the herbicidal action on the individual target plants. Further shared properties or similarities between the active compounds (B) are mentioned below.

Some of the compounds (B) belong to the same class of chemical compounds and/or have the same or a similar mechanism of action:

(B1.1) thiencarbazone and its esters and salts belong to the class of chemical compounds of the triazolone herbicides and are inhibitors of acetolactate synthase in plants (ALS inhibitors).

(B1.2) tembotrione and its salts belong to the class of chemical compounds of the benzoylcyclohexanediones and are inhibitors of hydroxyphenylpyruvate dioxygenase in plants (HPPD inhibitors).

(B1.3) SYN-523 belongs to the class of chemical compounds of the uracils (pyrimidinediones) and is an inhibitor of protoporphyrinogen oxidase in plants (PPO inhibitor).

(B1.4) pyroxsulam and (B1.5) penoxsulam and their salts belong to the class of chemical compounds of the triazolopyrimidines and are inhibitors of acetolactate synthase in plants (ALS inhibitors).

(B1.6) SYN-449 and its salts belong to the class of chemical compounds of the (bridged) benzoylcyclohexanediones and are inhibitors of hydroxyphenylpyruvate dioxygenase in plants (HPPD inhibitors).

(B2.1) pyrasulfotole and its salts belong to the class of chemical compounds of the benzoylpyrazoles, which are related to the benzoylcyclohexanediones, and are inhibitors of hydroxyphenylpyruvate dioxygenase in plants (HPPD inhibitors).

(B2.2) trifloxysulfuron and its salts belong to the class of chemical compounds of the pyridylsulfonylureas and are inhibitors of acetolactate synthase in plants (ALS inhibitors).

(B2.3) saflufenacil and its salts belong to the class of chemical compounds of the uracils (pyrimidinediones) and are inhibitors of protoporphyrinogen oxidase in plants (PPO inhibitors).

(B2.4) aminopyralid and its salts belong to the class of chemical compounds of the pyridylcarboxylic acids (picolinic acids) and are synthetic auxins in plants.

(B2.5) ethofumesate belongs to the class of chemical compounds of the benzofuranylmethanesulfonates and is an inhibitor of lipid synthesis in plants.

(B2.6) aminocyclopyrachlor and its salts or esters belong to the chemical class of the pyrimidinecarboxylic acids and are synthetic auxins in plants.

(B3.1) pyroxasulfone belongs to the class of chemical compounds of the oxazolinesulfonylmethylpyrazoles and is an inhibitor of the synthesis of long-chain fatty acids (inhibitor of very long chain fatty acid (VLCFA) elongases) in plants.

From the combinations defined above, preference is given to those which comprise one or more herbicides from group (A), preferably one herbicide (A) or a plurality of herbicides (A) which have the same chemical constitution and one or more herbicides from group (B), preferably one herbicide (B) or one or more herbicides (B) from the same subgroup (B1), (B2) or (B3).

Furthermore, the combinations according to the invention may be used together with other active compounds, such as the active compounds mentioned (herbicides, fungicides, insecticides, acaricides, etc.) and/or plant growth regulators or auxiliaries from the group of the additives, such as adjuvants and formulation auxiliaries, customary in crop protection. The combination of crop protection agents which comprise the active compounds (A) and (B) and, if appropriate, further active compounds are referred to here in short as "herbicide combination". Their use forms such as formulations or tank mixes represent herbicidal compositions.

Accordingly, the invention also provides the herbicidal compositions which comprise the active compound combinations according to the invention together with additives, such as adjuvants and formulation auxiliaries, customary in crop protection, and if appropriate further crop protection agents.

The invention also provides the use or the application method where the active compound combinations according to the invention are used as herbicides and plant growth regulators, preferably as herbicides and plant growth regulators comprising a synergistically effective amount of the respective active compound combination contained therein.

The application rates of the herbicides (B) are known in principle and are generally in the range from 0.01 g to 1000 g of AS/ha (g of AS/ha=g of active substance per hectare), preferably in the range from 0.02 g to 800 g of AS/ha, particularly in the range from 0.1 to 500 g of AS/ha.

In the mixtures according to the invention, in the context of the application rates mentioned, in general lower application rates of the active compound in question are required compared to the individual application. For the active compounds from group (B1), the application rate is preferably in the range of from 0.1 to 500 g of AS/ha, in particular in the range of from 0.2 to 250 g/ha. For the active compounds from group (B2), the application rate is preferably in the range of from 0.1 to 1000 g of AS/ha, in particular in the range of from 0.2 to 750 g/ha. For the active compound from group (B3), the application rate is preferably in the range of from 0.1 to 500 g of AS/ha, in particular in the range of from 0.2 to 200 g/ha. The Table 2 below states preferred and especially preferred application rates for the individual active compounds (B).

The weight ratios (A):(B) are, depending on the effective application rates, generally in the range from 1:100000 to 2000:1, preferably 1:40000 to 750:1, and particularly in the range from 1:15000 to 500:1. For the active compounds from groups (B1), (B2) and (B3), the preferred weight ratios (A):(B) are as follows:

(A):(B1) is preferably in the range of from 1:50000 to 2000:1, in particular from 1:13000 to 750:1;

(A):(B2) is preferably in the range of from 1:100000 to 2000:1, in particular from 1:40000 to 750:1;

(A):(B3) is preferably in the range of from 1:50000 to 2000:1, in particular from 1:18000 to 75:1.

Table 2 below states preferred and especially preferred ratios (A):(B) for the individual active compounds (B).

Specific herbicide combinations (Aa)+(Bb) are listed in Table 3 and are referred to there by the term Ka.b, where a is the respective code (=code a) from the number (Aa) of the herbicide (A) from Table 1 [=codes 1 to 127 of the compounds (A1) to (A127)] and b is the respective code (=code b) of the herbicide component (B) according to Table 2 below [=codes 1 to 24 of the compounds (B1.1) to (B3.1)]:

TABLE 2

Codes b for the herbicide component (B), preferred application rates with respect to (B) and preferred ratios (A):(B)

| Code b | Comp. (B) | Short name | Application rate [g of AS/ha] | Weight ratio (A):(B) |
|---|---|---|---|---|
| 1 | (B1.1) | thiencarbazone and its esters and salts | 0.1 to 200 (0.2 to 100) | 1:20000 to 2000:1 (1:10000 to 750:1) |
| 2 | (B1.1.1) | thiencarbazone | 0.1 to 200 (0.2 to 100) | 1:20000 to 2000:1 (1:10000 to 750:1) |
| 3 | (B1.1.2) | thiencarbazone-methyl | 0.1 to 200 (0.2 to 100) | 1:20000 to 2000:1 (1:10000 to 750:1) |
| 4 | (B1.1.3) | thiencarbazone-methyl-sodium | 0.1 to 200 (0.2 to 100) | 1:20000 to 2000:1 (1:10000 to 750:1) |
| 5 | (B1.2) | tembotrione and its salts | 0.1 to 500 (2 to 200) | 1:50000 to 200:1 (1:10000 to 75:1) |
| 6 | (B1.2.1) | tembotrione | 0.1 to 500 (2 to 200) | 1:50000 to 200:1 (1:10000 to 75:1) |

TABLE 2-continued

Codes b for the herbicide component (B), preferred application rates with respect to (B) and preferred ratios (A):(B)

| Code b | Comp. (B) | Short name | Application rate [g of AS/ha] | Weight ratio (A):(B) |
|---|---|---|---|---|
| 7 | (B1.3) | SYN-523 | 0.1 to 500 (2 to 200) | 1:50000 to 20000:1 (1:13000 to 750:1) |
| 8 | (B1.4) | pyroxsulam and its salts | 1 to 200 (2 to 150) | 1:20000 to 200:1 (1:7500 to 75:1) |
| 9 | (B1.4.1) | pyroxsulam | 1 to 200 (2 to 150) | 1:20000 to 200:1 (1:7500 to 75:1) |
| 10 | (B1.5) | penoxsulam and its salts | 1 to 200 (2 to 150) | 1:20000 to 200:1 (1:7500 to 75:1) |
| 11 | (B1.5.1) | penoxsulam | 1 to 200 (2 to 150) | 1:20000 to 200:1 (1:7500 to 75:1) |
| 12 | (B1.6) | SYN-449 and its salts | 1 to 200 (2 to 150) | 1:20000 to 200:1 (1:7500 to 75:1) |
| 13 | (B1.6.1) | SYN-449 | 1 to 200 (2 to 150) | 1:20000 to 200:1 (1:7500 to 75:1) |
| 14 | (B2.1) | pyrasulfotole and its salts | 1 to 300 (2 to 150) | 1:30000 to 200:1 (1:10000 to 30:1) |
| 15 | (B2.1.1) | pyrasulfotole | 1 to 300 (2 to 150) | 1:30000 to 200:1 (1:10000 to 30:1) |
| 16 | (B2.2) | trifloxysulfuron and its salts | 0.1 to 300 (0.2 to 150) | 1:30000 to 2000:1 (1:7500 to 300:1) |
| 17 | (B2.2.1) | trifloxysulfuron | 0.1 to 300 (0.2 to 150) | 1:30000 to 2000:1 (1:7500 to 300:1) |
| 18 | (B2.2.2) | trifloxysulfuron-sodium salt | 0.1 to 300 (0.2 to 150) | 1:30000 to 2000:1 (1:7500 to 300:1) |
| 19 | (B2.3) | saflufenacil and its salts | 0.1 to 300 (0.2 to 250) | 1:30000 to 2000:1 (1:12500 to 750:1) |
| 20 | (B2.3.1) | saflufenacil | 0.1 to 300 (0.2 to 250) | 1:30000 to 2000:1 (1:12500 to 750:1) |
| 21 | (B2.4) | aminopyralid and its salts | 0.1 to 300 (0.2 to 250) | 1:30000 to 2000:1 (1:12500 to 750:1) |
| 22 | (B2.4.1) | aminopyralid | 0.1 to 300 (0.2 to 250) | 1:30000 to 2000:1 (1:12500 to 750:1) |
| 23 | (B2.5) | ethofumesate | 1 to 1000 (2 to 750) | 1:100000 to 200:1 (1:37500 to 75:1) |
| 24 | (B2.6) | aminocyclopyra-chlor and its salts and esters | 1 to 1000 (2 to 350) | 1:75000 to 200:1 (1:25000 to 75:1) |
| 25 | (B2.6.1) | aminocyclopyra-chlor | 1 to 1000 (2 to 350) | 1:75000 to 200:1 (1:25000 to 75:1) |
| 26 | (B2.6.2) | aminocyclopyra-chlor potassium salt | 1 to 1000 (2 to 350) | 1:75000 to 200:1 (1:25000 to 75:1) |
| 27 | (B2.6.3) | aminocyclopyra-chlor sodium salt | 1 to 1000 (2 to 350) | 1:75000 to 200:1 (1:25000 to 75:1) |
| 28 | (B2.6.4) | aminocyclopyra-chlo rmethyl ester | 1 to 1000 (2 to 350) | 1:75000 to 200:1 (1:25000 to 75:1) |
| 29 | (B3.1) | pyroxasulfone | 0.1 to 500 (0.2 to 200) | 1:50000 to 200:1 (1:17500 to 75:1) |

Abbreviations for Table 2:

Comp. = component, active compound

AS = active substance (based on 100% active compound)

(A):(B) = ratio of the active compounds (A):(B) [(A) = Comp. (I) or preferably according to Tab. 1; (B) = Comp. according to Tab. 2]

The columns "Application rates" and "Weight ratios" in Table 2 contain in each case preferred and particularly preferred application rates (the latter in brackets) and "Weight ratios (A):(B)" based on the active compound group (B) or the active compound according to code b.

Preference is given to binary combinations comprising a herbicide from the group of the herbicides (A1) to (A127) and herbicides from the group (B1) or (B2) or (B3), for example a herbicide from the group of the herbicides (A1) to (A127) and one or more herbicides from the group (B1.1), (B1.1.1), (B1.1.2), (B1.1.3), (B1.2), (B1.2.1), (B1.3), (B1.4), (B1.4.1), (B1.5), (B1.5.1), (B1.6), (B1.6.1), (B2.1), (B2.1.1), (B2.2), (B2.2.1), (B2.2.2), (B2.3), (B2.3.1), (B2.4), (B2.4.1), (B2.5), (B2.6), (B2.6.1), (B2.6.2), (B2.6.3), (B2.6.4) and(B3.1), specifically one of the combinations from Table 3.

TABLE 3

Binary herbicide combinations of the active compounds (A) and (B)

K1.1, K1.2, K1.3, K1.4, K1.5, K1.6, K1.7, K1.8, K1.9, K1.10, K1.11, K1.12, K1.13, K1.14, K1.15, K1.16, K1.17, K1.18, K1.19, K1.20, K1.21, K1.22, K1.23, K1.24, K1.25, K1.26, K1.27, K1.28, K1.29,
K2.1, K2.2, K2.3, K2.4, K2.5, K2.6, K2.7, K2.8, K2.9, K2.10, K2.11, K2.12, K2.13, K2.14, K2.15, K2.16, K2.17, K2.18, K2.19, K2.20, K2.21, K2.22, K2.23, K2.24, K2.25, K2.26, K2.27, K2.28, K2.29,
K3.1, K3.2, K3.3, K3.4, K3.5, K3.6, K3.7, K3.8, K3.9, K3.10, K3.11, K3.12, K3.13, K3.14, K3.15, K3.16, K3.17, K3.18, K3.19, K3.20, K3.21, K3.22, K3.23, K3.24, K3.25, K3.26, K3.27, K3.28, K3.29,
K4.1, K4.2, K4.3, K4.4, K4.5, K4.6, K4.7, K4.8, K4.9, K4.10, K4.11, K4.12, K4.13, K4.14, K4.15, K4.16, K4.17, K4.18, K4.19, K4.20, K4.21, K4.22, K4.23, K4.24, K4.25, K4.26, K4.27, K4.28, K4.29,
K5.1, K5.2, K5.3, K5.4, K5.5, K5.6, K5.7, K5.8, K5.9, K5.10, K5.11, K5.12, K5.13, K5.14, K5.15, K5.16, K5.17, K5.18, K5.19, K5.20, K5.21, K5.22, K5.23, K5.24, K5.25, K5.26, K5.27, K5.28, K5.29,
K6.1, K6.2, K6.3, K6.4, K6.5, K6.6, K6.7, K6.8, K6.9, K6.10, K6.11, K6.12, K6.13, K6.14, K6.15, K6.16, K6.17, K6.18, K6.19, K6.20, K6.21, K6.22, K6.23, K6.24, K6.25, K6.26, K6.27, K6.28, K6.29,
K7.1, K7.2, K7.3, K7.4, K7.5, K7.6, K7.7, K7.8, K7.9, K7.10, K7.11, K7.12, K7.13, K7.14, K7.15, K7.16, K7.17, K7.18, K7.19, K7.20, K7.21, K7.22, K7.23, K7.24, K7.25, K7.26, K7.27, K7.28, K7.29,
K8.1, K8.2, K8.3, K8.4, K8.5, K8.6, K8.7, K8.8, K8.9, K8.10, K8.11, K8.12, K8.13, K8.14, K8.15, K8.16, K8.17, K8.18, K8.19, K8.20, K8.21, K8.22, K8.23, K8.24, K8.25, K8.26, K8.27, K8.28, K8.29,
K9.1, K9.2, K9.3, K9.4, K9.5, K9.6, K9.7, K9.8, K9.9, K9.10, K9.11, K9.12, K9.13, K9.14, K9.15, K9.16, K9.17, K9.18, K9.19, K9.20, K9.21, K9.22, K9.23, K9.24, K9.25, K9.26, K9.27, K9.28, K9.29,
K10.1, K10.2, K10.3, K10.4, K10.5, K10.6, K10.7, K10.8, K10.9, K10.10, K10.11, K10.12, K10.13, K10.14, K10.15, K10.16, K10.17, K10.18, K10.19, K10.20, K10.21, K10.22, K10.23, K10.24, K10.25, K10.26, K10.27, K10.28, K10.29,
K11.1, K11.2, K11.3, K11.4, K11.5, K11.6, K11.7, K11.8, K11.9, K11.10, K11.11, K11.12, K11.13, K11.14, K11.15, K11.16, K11.17, K11.18, K11.19, K11.20, K11.21, K11.22, K11.23, K11.24, K11.25, K11.26, K11.27, K11.28, K11.29,
K12.1, K12.2, K12.3, K12.4, K12.5, K12.6, K12.7, K12.8, K12.9, K12.10, K12.11, K12.12, K12.13, K12.14, K12.15, K12.16, K12.17, K12.18, K12.19, K12.20, K12.21, K12.22, K12.23, K12.24, K12.25, K12.26, K12.27, K12.28, K12.29,
K13.1, K13.2, K13.3, K13.4, K13.5, K13.6, K13.7, K13.8, K13.9, K13.10, K13.11, K13.12, K13.13, K13.14, K13.15, K13.16, K13.17, K13.18, K13.19, K13.20, K13.21, K13.22, K13.23, K13.24, K13.25, K13.26, K13.27, K13.28, K13.29,
K14.1, K14.2, K14.3, K14.4, K14.5, K14.6, K14.7, K14.8, K14.9, K14.10, K14.11, K14.12, K14.13, K14.14, K14.15, K14.16, K14.17, K14.18, K14.19, K14.20, K14.21, K14.22, K14.23, K14.24, K14.25, K14.26, K14.27, K14.28, K14.29,
K15.1, K15.2, K15.3, K15.4, K15.5, K15.6, K15.7, K15.8, K15.9, K15.10, K15.11, K15.12, K15.13, K15.14, K15.15, K15.16, K15.17, K15.18, K15.19, K15.20, K15.21, K15.22, K15.23, K15.24, K15.25, K15.26, K15.27, K15.28, K15.29,
K16.1, K16.2, K16.3, K16.4, K16.5, K16.6, K16.7, K16.8, K16.9, K16.10, K16.11, K16.12, K16.13, K16.14, K16.15, K16.16, K16.17, K16.18, K16.19, K16.20, K16.21, K16.22, K16.23, K16.24, K16.25, K16.26, K16.27, K16.28, K16.29,
K17.1, K17.2, K17.3, K17.4, K17.5, K17.6, K17.7, K17.8, K17.9, K17.10, K17.11, K17.12, K17.13, K17.14, K17.15, K17.16, K17.17, K17.18, K17.19, K17.20, K17.21, K17.22, K17.23, K17.24, K17.25, K17.26, K17.27, K17.28, K17.29,
K18.1, K18.2, K18.3, K18.4, K18.5, K18.6, K18.7, K18.8, K18.9, K18.10, K18.11, K18.12, K18.13, K18.14, K18.15, K18.16, K18.17, K18.18, K18.19, K18.20, K18.21, K18.22, K18.23, K18.24, K18.25, K18.26, K18.27, K18.28, K18.29,
K19.1, K19.2, K19.3, K19.4, K19.5, K19.6, K19.7, K19.8, K19.9, K19.10, K19.11, K19.12, K19.13, K19.14, K19.15, K19.16, K19.17, K19.18, K19.19, K19.20, K19.21, K19.22, K19.23, K19.24, K19.25, K19.26, K19.27, K19.28, K19.29,
K20.1, K20.2, K20.3, K20.4, K20.5, K20.6, K20.7, K20.8, K20.9, K20.10, K20.11, K20.12, K20.13, K20.14, K20.15, K20.16, K20.17, K20.18, K20.19, K20.20, K20.21, K20.22, K20.23, K20.24, K20.25, K20.26, K20.27, K20.28, K20.29,
K21.1, K21.2, K21.3, K21.4, K21.5, K21.6, K21.7, K21.8, K21.9, K21.10, K21.11, K21.12, K21.13, K21.14, K21.15, K21.16, K21.17, K21.18, K21.19, K21.20, K21.21, K21.22, K21.23, K21.24, K21.25, K21.26, K21.27, K21.28, K21.29,

TABLE 3-continued

Binary herbicide combinations of the active compounds (A) and (B)

K22.1, K22.2, K22.3, K22.4, K22.5, K22.6, K22.7, K22.8, K22.9, K22.10, K22.11, K22.12, K22.13, K22.14, K22.15, K22.16, K22.17, K22.18, K22.19, K22.20, K22.21, K22.22, K22.23, K22.24, K22.25, K22.26, K22.27, K22.28, K22.29,
K23.1, K23.2, K23.3, K23.4, K23.5, K23.6, K23.7, K23.8, K23.9, K23.10, K23.11, K23.12, K23.13, K23.14, K23.15, K23.16, K23.17, K23.18, K23.19, K23.20, K23.21, K23.22, K23.23, K23.24, K23.25, K23.26, K23.27, K23.28, K23.29,
K24.1, K24.2, K24.3, K24.4, K24.5, K24.6, K24.7, K24.8, K24.9, K24.10, K24.11, K24.12, K24.13, K24.14, K24.15, K24.16, K24.17, K24.18, K24.19, K24.20, K24.21, K24.22, K24.23, K24.24, K24.25, K24.26, K24.27, K24.28, K24.29,
K25.1, K25.2, K25.3, K25.4, K25.5, K25.6, K25.7, K25.8, K25.9, K25.10, K25.11, K25.12, K25.13, K25.14, K25.15, K25.16, K25.17, K25.18, K25.19, K25.20, K25.21, K25.22, K25.23, K25.24, K25.25, K25.26, K25.27, K25.28, K25.29,
K26.1, K26.2, K26.3, K26.4, K26.5, K26.6, K26.7, K26.8, K26.9, K26.10, K26.11, K26.12, K26.13, K26.14, K26.15, K26.16, K26.17, K26.18, K26.19, K26.20, K26.21, K26.22, K26.23, K26.24, K26.25, K26.26, K26.27, K26.28, K26.29,
K27.1, K27.2, K27.3, K27.4, K27.5, K27.6, K27.7, K27.8, K27.9, K27.10, K27.11, K27.12, K27.13, K27.14, K27.15, K27.16, K27.17, K27.18, K27.19, K27.20, K27.21, K27.22, K27.23, K27.24, K27.25, K27.26, K27.27, K27.28, K27.29,
K28.1, K28.2, K28.3, K28.4, K28.5, K28.6, K28.7, K28.8, K28.9, K28.10, K28.11, K28.12, K28.13, K28.14, K28.15, K28.16, K28.17, K28.18, K28.19, K28.20, K28.21, K28.22, K28.23, K28.24, K28.25, K28.26, K28.27, K28.28, K28.29,
K29.1, K29.2, K29.3, K29.4, K29.5, K29.6, K29.7, K29.8, K29.9, K29.10, K29.11, K29.12, K29.13, K29.14, K29.15, K29.16, K29.17, K29.18, K29.19, K29.20, K29.21, K29.22, K29.23, K29.24, K29.25, K29.26, K29.27, K29.28, K29.29,
K30.1, K30.2, K30.3, K30.4, K30.5, K30.6, K30.7, K30.8, K30.9, K30.10, K30.11, K30.12, K30.13, K30.14, K30.15, K30.16, K30.17, K30.18, K30.19, K30.20, K30.21, K30.22, K30.23, K30.24, K30.25, K30.26, K30.27, K30.28, K30.29,
K31.1, K31.2, K31.3, K31.4, K31.5, K31.6, K31.7, K31.8, K31.9, K31.10, K31.11, K31.12, K31.13, K31.14, K31.15, K31.16, K31.17, K31.18, K31.19, K31.20, K31.21, K31.22, K31.23, K31.24, K31.25, K31.26, K31.27, K31.28, K31.29,
K32.1, K32.2, K32.3, K32.4, K32.5, K32.6, K32.7, K32.8, K32.9, K32.10, K32.11, K32.12, K32.13, K32.14, K32.15, K32.16, K32.17, K32.18, K32.19, K32.20, K32.21, K32.22, K32.23, K32.24, K32.25, K32.26, K32.27, K32.28, K32.29,
K33.1, K33.2, K33.3, K33.4, K33.5, K33.6, K33.7, K33.8, K33.9, K33.10, K33.11, K33.12, K33.13, K33.14, K33.15, K33.16, K33.17, K33.18, K33.19, K33.20, K33.21, K33.22, K33.23, K33.24, K33.25, K33.26, K33.27, K33.28, K33.29,
K34.1, K34.2, K34.3, K34.4, K34.5, K34.6, K34.7, K34.8, K34.9, K34.10, K34.11, K34.12, K34.13, K34.14, K34.15, K34.16, K34.17, K34.18, K34.19, K34.20, K34.21, K34.22, K34.23, K34.24, K34.25, K34.26, K34.27, K34.28, K34.29,
K35.1, K35.2, K35.3, K35.4, K35.5, K35.6, K35.7, K35.8, K35.9, K35.10, K35.11, K35.12, K35.13, K35.14, K35.15, K35.16, K35.17, K35.18, K35.19, K35.20, K35.21, K35.22, K35.23, K35.24, K35.25, K35.26, K35.27, K35.28, K35.29,
K36.1, K36.2, K36.3, K36.4, K36.5, K36.6, K36.7, K36.8, K36.9, K36.10, K36.11, K36.12, K36.13, K36.14, K36.15, K36.16, K36.17, K36.18, K36.19, K36.20, K36.21, K36.22, K36.23, K36.24, K36.25, K36.26, K36.27, K36.28, K36.29,
K37.1, K37.2, K37.3, K37.4, K37.5, K37.6, K37.7, K37.8, K37.9, K37.10, K37.11, K37.12, K37.13, K37.14, K37.15, K37.16, K37.17, K37.18, K37.19, K37.20, K37.21, K37.22, K37.23, K37.24, K37.25, K37.26, K37.27, K37.28, K37.29,
K38.1, K38.2, K38.3, K38.4, K38.5, K38.6, K38.7, K38.8, K38.9, K38.10, K38.11, K38.12, K38.13, K38.14, K38.15, K38.16, K38.17, K38.18, K38.19, K38.20, K38.21, K38.22, K38.23, K38.24, K38.25, K38.26, K38.27, K38.28, K38.29,
K39.1, K39.2, K39.3, K39.4, K39.5, K39.6, K39.7, K39.8, K39.9, K39.10, K39.11, K39.12, K39.13, K39.14, K39.15, K39.16, K39.17, K39.18, K39.19, K39.20, K39.21, K39.22, K39.23, K39.24, K39.25, K39.26, K39.27, K39.28, K39.29,
K40.1, K40.2, K40.3, K40.4, K40.5, K40.6, K40.7, K40.8, K40.9, K40.10, K40.11, K40.12, K40.13, K40.14, K40.15, K40.16, K40.17, K40.18, K40.19, K40.20, K40.21, K40.22, K40.23, K40.24, K40.25, K40.26, K40.27, K40.28, K40.29,
K41.1, K41.2, K41.3, K41.4, K41.5, K41.6, K41.7, K41.8, K41.9, K41.10, K41.11, K41.12, K41.13, K41.14, K41.15, K41.16, K41.17, K41.18, K41.19, K41.20, K41.21, K41.22, K41.23, K41.24, K41.25, K41.26, K41.27, K41.28, K41.29,
K42.1, K42.2, K42.3, K42.4, K42.5, K42.6, K42.7, K42.8, K42.9, K42.10, K42.11, K42.12, K42.13, K42.14, K42.15, K42.16, K42.17, K42.18, K42.19, K42.20, K42.21, K42.22, K42.23, K42.24, K42.25, K42.26, K42.27, K42.28, K42.29,
K43.1, K43.2, K43.3, K43.4, K43.5, K43.6, K43.7, K43.8, K43.9, K43.10, K43.11, K43.12, K43.13, K43.14, K43.15, K43.16, K43.17, K43.18, K43.19, K43.20, K43.21, K43.22, K43.23, K43.24, K43.25, K43.26, K43.27, K43.28, K43.29,
K44.1, K44.2, K44.3, K44.4, K44.5, K44.6, K44.7, K44.8, K44.9, K44.10, K44.11, K44.12, K44.13, K44.14, K44.15, K44.16, K44.17, K44.18, K44.19, K44.20, K44.21, K44.22, K44.23, K44.24, K44.25, K44.26, K44.27, K44.28, K44.29,
K45.1, K45.2, K45.3, K45.4, K45.5, K45.6, K45.7, K45.8, K45.9, K45.10, K45.11, K45.12, K45.13, K45.14, K45.15, K45.16, K45.17, K45.18, K45.19, K45.20, K45.21, K45.22, K45.23, K45.24, K45.25, K45.26, K45.27, K45.28, K45.29,
K46.1, K46.2, K46.3, K46.4, K46.5, K46.6, K46.7, K46.8, K46.9, K46.10, K46.11, K46.12, K46.13, K46.14, K46.15, K46.16, K46.17, K46.18, K46.19, K46.20, K46.21, K46.22, K46.23, K46.24, K46.25, K46.26, K46.27, K46.28, K46.29,
K47.1, K47.2, K47.3, K47.4, K47.5, K47.6, K47.7, K47.8, K47.9, K47.10, K47.11, K47.12, K47.13, K47.14, K47.15, K47.16, K47.17, K47.18, K47.19, K47.20, K47.21, K47.22, K47.23, K47.24, K47.25, K47.26, K47.27, K47.28, K47.29,
K48.1, K48.2, K48.3, K48.4, K48.5, K48.6, K48.7, K48.8, K48.9, K48.10, K48.11, K48.12, K48.13, K48.14, K48.15, K48.16, K48.17, K48.18, K48.19, K48.20, K48.21, K48.22, K48.23, K48.24, K48.25, K48.26, K48.27, K48.28, K48.29,
K49.1, K49.2, K49.3, K49.4, K49.5, K49.6, K49.7, K49.8, K49.9, K49.10, K49.11, K49.12, K49.13, K49.14, K49.15, K49.16, K49.17, K49.18, K49.19, K49.20, K49.21, K49.22, K49.23, K49.24, K49.25, K49.26, K49.27, K49.28, K49.29,
K50.1, K50.2, K50.3, K50.4, K50.5, K50.6, K50.7, K50.8, K50.9, K50.10, K50.11, K50.12, K50.13, K50.14, K50.15, K50.16, K50.17, K50.18, K50.19, K50.20, K50.21, K50.22, K50.23, K50.24, K50.25, K50.26, K50.27, K50.28, K50.29,
K51.1, K51.2, K51.3, K51.4, K51.5, K51.6, K51.7, K51.8, K51.9, K51.10, K51.11, K51.12, K51.13, K51.14, K51.15, K51.16, K51.17, K51.18, K51.19, K51.20, K51.21, K51.22, K51.23, K51.24, K51.25, K51.26, K51.27, K51.28, K51.29,
K52.1, K52.2, K52.3, K52.4, K52.5, K52.6, K52.7, K52.8, K52.9, K52.10, K52.11, K52.12, K52.13, K52.14, K52.15, K52.16, K52.17, K52.18, K52.19, K52.20, K52.21, K52.22, K52.23, K52.24, K52.25, K52.26, K52.27, K52.28, K52.29,
K53.1, K53.2, K53.3, K53.4, K53.5, K53.6, K53.7, K53.8, K53.9, K53.10, K53.11, K53.12, K53.13, K53.14, K53.15, K53.16, K53.17, K53.18, K53.19, K53.20, K53.21, K53.22, K53.23, K53.24, K53.25, K53.26, K53.27, K53.28, K53.29,
K54.1, K54.2, K54.3, K54.4, K54.5, K54.6, K54.7, K54.8, K54.9, K54.10, K54.11, K54.12, K54.13, K54.14, K54.15, K54.16, K54.17, K54.18, K54.19, K54.20, K54.21, K54.22, K54.23, K54.24, K54.25, K54.26, K54.27, K54.28, K54.29,
K55.1, K55.2, K55.3, K55.4, K55.5, K55.6, K55.7, K55.8, K55.9, K55.10, K55.11, K55.12, K55.13, K55.14, K55.15, K55.16, K55.17, K55.18, K55.19, K55.20, K55.21, K55.22, K55.23, K55.24, K55.25, K55.26, K55.27, K55.28, K55.29,
K56.1, K56.2, K56.3, K56.4, K56.5, K56.6, K56.7, K56.8, K56.9, K56.10, K56.11, K56.12, K56.13, K56.14, K56.15, K56.16, K56.17, K56.18, K56.19, K56.20, K56.21, K56.22, K56.23, K56.24, K56.25, K56.26, K56.27, K56.28, K56.29,
K57.1, K57.2, K57.3, K57.4, K57.5, K57.6, K57.7, K57.8, K57.9, K57.10, K57.11, K57.12, K57.13, K57.14, K57.15, K57.16, K57.17, K57.18, K57.19, K57.20, K57.21, K57.22, K57.23, K57.24, K57.25, K57.26, K57.27, K57.28, K57.29,
K58.1, K58.2, K58.3, K58.4, K58.5, K58.6, K58.7, K58.8, K58.9, K58.10, K58.11, K58.12, K58.13, K58.14, K58.15, K58.16, K58.17, K58.18, K58.19, K58.20, K58.21, K58.22, K58.23, K58.24, K58.25, K58.26, K58.27, K58.28, K58.29,
K59.1, K59.2, K59.3, K59.4, K59.5, K59.6, K59.7, K59.8, K59.9, K59.10, K59.11, K59.12, K59.13, K59.14, K59.15, K59.16, K59.17, K59.18, K59.19, K59.20, K59.21, K59.22, K59.23, K59.24, K59.25, K59.26, K59.27, K59.28, K59.29,
K60.1, K60.2, K60.3, K60.4, K60.5, K60.6, K60.7, K60.8, K60.9, K60.10, K60.11, K60.12, K60.13, K60.14, K60.15, K60.16, K60.17, K60.18, K60.19, K60.20, K60.21, K60.22, K60.23, K60.24, K60.25, K60.26, K60.27, K60.28, K60.29,

TABLE 3-continued

Binary herbicide combinations of the active compounds (A) and (B)

K61.1, K61.2, K61.3, K61.4, K61.5, K61.6, K61.7, K61.8, K61.9, K61.10, K61.11, K61.22, K61.23, K61.24, K61.25, K61.26, K61.27, K61.28, K61.29,
K62.1, K62.2, K62.3, K62.4, K62.5, K62.6, K62.7, K62.8, K62.9, K62.10, K62.11, K62.12, K62.13, K62.14, K62.15, K62.16, K62.17, K62.18, K62.19, K62.20, K62.21, K62.22, K62.23, K62.24, K62.25, K62.26, K62.27, K62.28, K62.29,
K63.1, K63.2, K63.3, K63.4, K63.5, K63.6, K63.7, K63.8, K63.9, K63.10, K63.11, K63.12, K63.13, K63.14, K63.15, K63.16, K63.17, K63.18, K63.19, K63.20, K63.21, K63.22, K63.23, K63.24, K63.25, K63.26, K63.27, K63.28, K63.29,
K64.1, K64.2, K64.3, K64.4, K64.5, K64.6, K64.7, K64.8, K64.9, K64.10, K64.11, K64.12, K64.13, K64.14, K64.15, K64.16, K64.17, K64.18, K64.19, K64.20, K64.21, K64.22, K64.23, K64.24, K64.25, K64.26, K64.27, K64.28, K64.29,
K65.1, K65.2, K65.3, K65.4, K65.5, K65.6, K65.7, K65.8, K65.9, K65.10, K65.11, K65.12, K65.13, K65.14, K65.15, K65.16, K65.17, K65.18, K65.19, K65.20, K65.21, K65.22, K65.23, K65.24, K65.25, K65.26, K65.27, K65.28, K65.29,
K66.1, K66.2, K66.3, K66.4, K66.5, K66.6, K66.7, K66.8, K66.9, K66.10, K66.11, K66.12, K66.13, K66.14, K66.15, K66.16, K66.17, K66.18, K66.19, K66.20, K66.21, K66.22, K66.23, K66.24, K66.25, K66.26, K66.27, K66.28, K66.29,
K67.1, K67.2, K67.3, K67.4, K67.5, K67.6, K67.7, K67.8, K67.9, K67.10, K67.11, K67.12, K67.13, K67.14, K67.15, K67.16, K67.17, K67.18, K67.19, K67.20, K67.21, K67.22, K67.23, K67.24, K67.25, K67.26, K67.27, K67.28, K67.29,
K68.1, K68.2, K68.3, K68.4, K68.5, K68.6, K68.7, K68.8, K68.9, K68.10, K68.11, K68.12, K68.13, K68.14, K68.15, K68.16, K68.17, K68.18, K68.19, K68.20, K68.21, K68.22, K68.23, K68.24, K68.25, K68.26, K68.27, K68.28, K68.29,
K69.1, K69.2, K69.3, K69.4, K69.5, K69.6, K69.7, K69.8, K69.9, K69.10, K69.11, K69.12, K69.13, K69.14, K69.15, K69.16, K69.17, K69.18, K69.19, K69.20, K69.21, K69.22, K69.23, K69.24, K69.25, K69.26, K69.27, K69.28, K69.29,
K70.1, K70.2, K70.3, K70.4, K70.5, K70.6, K70.7, K70.8, K70.9, K70.10, K70.11, K70.12, K70.13, K70.14, K70.15, K70.16, K70.17, K70.18, K70.19, K70.20, K70.21, K70.22, K70.23, K70.24, K70.25, K70.26, K70.27, K70.28, K70.29,
K71.1, K71.2, K71.3, K71.4, K71.5, K71.6, K71.7, K71.8, K71.9, K71.10, K71.11, K71.12, K71.13, K71.14, K71.15, K71.16, K71.17, K71.18, K71.19, K71.20, K71.21, K71.22, K71.23, K71.24, K71.25, K71.26, K71.27, K71.28, K71.29,
K72.1, K72.2, K72.3, K72.4, K72.5, K72.6, K72.7, K72.8, K72.9, K72.10, K72.11, K72.12, K72.13, K72.14, K72.15, K72.16, K72.17, K72.18, K72.19, K72.20, K72.21, K72.22, K72.23, K72.24, K72.25, K72.26, K72.27, K72.28, K72.29,
K73.1, K73.2, K73.3, K73.4, K73.5, K73.6, K73.7, K73.8, K73.9, K73.10, K73.11, K73.12, K73.13, K73.14, K73.15, K73.16, K73.17, K73.18, K73.19, K73.20, K73.21, K73.22, K73.23, K73.24, K73.25, K73.26, K73.27, K73.28, K73.29,
K74.1, K74.2, K74.3, K74.4, K74.5, K74.6, K74.7, K74.8, K74.9, K74.10, K74.11, K74.12, K74.13, K74.14, K74.15, K74.16, K74.17, K74.18, K74.19, K74.20, K74.21, K74.22, K74.23, K74.24, K74.25, K74.26, K74.27, K74.28, K74.29,
K75.1, K75.2, K75.3, K75.4, K75.5, K75.6, K75.7, K75.8, K75.9, K75.10, K75.11, K75.12, K75.13, K75.14, K75.15, K75.16, K75.17, K75.18, K75.19, K75.20, K75.21, K75.22, K75.23, K75.24, K75.25, K75.26, K75.27, K75.28, K75.29,
K76.1, K76.2, K76.3, K76.4, K76.5, K76.6, K76.7, K76.8, K76.9, K76.10, K76.11, K76.12, K76.13, K76.14, K76.15, K76.16, K76.17, K76.18, K76.19, K76.20, K76.21, K76.22, K76.23, K76.24, K76.25, K76.26, K76.27, K76.28, K76.29,
K77.1, K77.2, K77.3, K77.4, K77.5, K77.6, K77.7, K77.8, K77.9, K77.10, K77.11, K77.12, K77.13, K77.14, K77.15, K77.16, K77.17, K77.18, K77.19, K77.20, K77.21, K77.22, K77.23, K77.24, K77.25, K77.26, K77.27, K77.28, K77.29,
K78.1, K78.2, K78.3, K78.4, K78.5, K78.6, K78.7, K78.8, K78.9, K78.10, K78.11, K78.12, K78.13, K78.14, K78.15, K78.16, K78.17, K78.18, K78.19, K78.20, K78.21, K78.22, K78.23, K78.24, K78.25, K78.26, K78.27, K78.28, K78.29,
K79.1, K79.2, K79.3, K79.4, K79.5, K79.6, K79.7, K79.8, K79.9, K79.10, K79.11, K79.12, K79.13, K79.14, K79.15, K79.16, K79.17, K79.18, K79.19, K79.20, K79.21, K79.22, K79.23, K79.24, K79.25, K79.26, K79.27, K79.28, K79.29,
K80.1, K80.2, K80.3, K80.4, K80.5, K80.6, K80.7, K80.8, K80.9, K80.10, K80.11, K80.12, K80.13, K80.14, K80.15, K80.16, K80.17, K80.18,

TABLE 3-continued

Binary herbicide combinations of the active compounds (A) and (B)

K80.19, K80.20, K80.21, K80.22, K80.23, K80.24, K80.25, K80.26, K80.27, K80.28, K80.29,
K81.1, K81.2, K81.3, K81.4, K81.5, K81.6, K81.7, K81.8, K81.9, K81.10, K81.11, K81.12, K81.13, K81.14, K81.15, K81.16, K81.17, K81.18, K81.19, K81.20, K81.21, K81.22, K81.23, K81.24, K81.25, K81.26, K81.27, K81.28, K81.29,
K82.1, K82.2, K82.3, K82.4, K82.5, K82.6, K82.7, K82.8, K82.9, K82.10, K82.11, K82.12, K82.13, K82.14, K82.15, K82.16, K82.17, K82.18, K82.19, K82.20, K82.21, K82.22, K82.23, K82.24, K82.25, K82.26, K82.27, K82.28, K82.29,
K83.1, K83.2, K83.3, K83.4, K83.5, K83.6, K83.7, K83.8, K83.9, K83.10, K83.11, K83.12, K83.13, K83.14, K83.15, K83.16, K83.17, K83.18, K83.19, K83.20, K83.21, K83.22, K83.23, K83.24, K83.25, K83.26, K83.27, K83.28, K83.29,
K84.1, K84.2, K84.3, K84.4, K84.5, K84.6, K84.7, K84.8, K84.9, K84.10, K84.11, K84.12, K84.13, K84.14, K84.15, K84.16, K84.17, K84.18, K84.19, K84.20, K84.21, K84.22, K84.23, K84.24, K84.25, K84.26, K84.27, K84.28, K84.29,
K85.1, K85.2, K85.3, K85.4, K85.5, K85.6, K85.7, K85.8, K85.9, K85.10, K85.11, K85.12, K85.13, K85.14, K85.15, K85.16, K85.17, K85.18, K85.19, K85.20, K85.21, K85.22, K85.23, K85.24, K85.25, K85.26, K85.27, K85.28, K85.29,
K86.1, K86.2, K86.3, K86.4, K86.5, K86.6, K86.7, K86.8, K86.9, K86.10, K86.11, K86.12, K86.13, K86.14, K86.15, K86.16, K86.17, K86.18, K86.19, K86.20, K86.21, K86.22, K86.23, K86.24, K86.25, K86.26, K86.27, K86.28, K86.29,
K87.1, K87.2, K87.3, K87.4, K87.5, K87.6, K87.7, K87.8, K87.9, K87.10, K87.11, K87.12, K87.13, K87.14, K87.15, K87.16, K87.17, K87.18, K87.19, K87.20, K87.21, K87.22, K87.23, K87.24, K87.25, K87.26, K87.27, K87.28, K87.29,
K88.1, K88.2, K88.3, K88.4, K88.5, K88.6, K88.7, K88.8, K88.9, K88.10, K88.11, K88.12, K88.13, K88.14, K88.15, K88.16, K88.17, K88.18, K88.19, K88.20, K88.21, K88.22, K88.23, K88.24, K88.25, K88.26, K88.27, K88.28, K88.29,
K89.1, K89.2, K89.3, K89.4, K89.5, K89.6, K89.7, K89.8, K89.9, K89.10, K89.11, K89.12, K89.13, K89.14, K89.15, K89.16, K89.17, K89.18, K89.19, K89.20, K89.21, K89.22, K89.23, K89.24, K89.25, K89.26, K89.27, K89.28, K89.29,
K90.1, K90.2, K90.3, K90.4, K90.5, K90.6, K90.7, K90.8, K90.9, K90.10, K90.11, K90.12, K90.13, K90.14, K90.15, K90.16, K90.17, K90.18, K90.19, K90.20, K90.21, K90.22, K90.23, K90.24, K90.25, K90.26, K90.27, K90.28, K90.29,
K91.1, K91.2, K91.3, K91.4, K91.5, K91.6, K91.7, K91.8, K91.9, K91.10, K91.11, K91.12, K91.13, K91.14, K91.15, K91.16, K91.17, K91.18, K91.19, K91.20, K91.21, K91.22, K91.23, K91.24, K91.25, K91.26, K91.27, K91.28, K91.29,
K92.1, K92.2, K92.3, K92.4, K92.5, K92.6, K92.7, K92.8, K92.9, K92.10, K92.11, K92.12, K92.13, K92.14, K92.15, K92.16, K92.17, K92.18, K92.19, K92.20, K92.21, K92.22, K92.23, K92.24, K92.25, K92.26, K92.27, K92.28, K92.29,
K93.1, K93.2, K93.3, K93.4, K93.5, K93.6, K93.7, K93.8, K93.9, K93.10, K93.11, K93.12, K93.13, K93.14, K93.15, K93.16, K93.17, K93.18, K93.19, K93.20, K93.21, K93.22, K93.23, K93.24, K93.25, K93.26, K93.27, K93.28, K93.29,
K94.1, K94.2, K94.3, K94.4, K94.5, K94.6, K94.7, K94.8, K94.9, K94.10, K94.11, K94.12, K94.13, K94.14, K94.15, K94.16, K94.17, K94.18, K94.19, K94.20, K94.21, K94.22, K94.23, K94.24, K94.25, K94.26, K94.27, K94.28, K94.29,
K95.1, K95.2, K95.3, K95.4, K95.5, K95.6, K95.7, K95.8, K95.9, K95.10, K95.11, K95.12, K95.13, K95.14, K95.15, K95.16, K95.17, K95.18, K95.19, K95.20, K95.21, K95.22, K95.23, K95.24, K95.25, K95.26, K95.27, K95.28, K95.29,
K96.1, K96.2, K96.3, K96.4, K96.5, K96.6, K96.7, K96.8, K96.9, K96.10, K96.11, K96.12, K96.13, K96.14, K96.15, K96.16, K96.17, K96.18, K96.19, K96.20, K96.21, K96.22, K96.23, K96.24, K96.25, K96.26, K96.27, K96.28, K96.29,
K97.1, K97.2, K97.3, K97.4, K97.5, K97.6, K97.7, K97.8, K97.9, K97.10, K97.11, K97.12, K97.13, K97.14, K97.15, K97.16, K97.17, K97.18, K97.19, K97.20, K97.21, K97.22, K97.23, K97.24, K97.25, K97.26, K97.27, K97.28, K97.29,
K98.1, K98.2, K98.3, K98.4, K98.5, K98.6, K98.7, K98.8, K98.9, K98.10, K98.11, K98.12, K98.13, K98.14, K98.15, K98.16, K98.17, K98.18, K98.19, K98.20, K98.21, K98.22, K98.23, K98.24, K98.25, K98.26, K98.27, K98.28, K98.29,
K99.1, K99.2, K99.3, K99.4, K99.5, K99.6, K99.7, K99.8, K99.9, K99.10, K99.11, K99.12, K99.13, K99.14, K99.15, K99.16, K99.17, K99.18, K99.19, K99.20, K99.21, K99.22, K99.23, K99.24, K99.25, K99.26, K99.27, K99.28, K99.29,

TABLE 3-continued

| Binary herbicide combinations of the active compounds (A) and (B) |
|---|
| K100.1, K100.2, K100.3, K100.4, K100.5, K100.6, K100.7, K100.8, K100.9, K100.10, K100.11, K100.12, K100.13, K100.14, K100.15, K100.16, K100.17, K100.18, K100.19, K100.20, K100.21, K100.22, K100.23, K100.24, K100.25, K100.26, K100.27, K100.28, K100.29, K101.1, K101.2, K101.3, K101.4, K101.5, K101.6, K101.7, K101.8, K101.9, K101.10, K101.11, K101.12, K101.13, K101.14, K101.15, K101.16, K101.17, K101.18, K101.19, K101.20, K101.21, K101.22, K101.23, K101.24, K101.25, K101.26, K101.27, K101.28, K101.29, K102.1, K102.2, K102.3, K102.4, K102.5, K102.6, K102.7, K102.8, K102.9, K102.10, K102.11, K102.12, K102.13, K102.14, K102.15, K102.16, K102.17, K102.18, K102.19, K102.20, K102.21, K102.22, K102.23, K102.24, K102.25, K102.26, K102.27, K102.28, K102.29, K103.1, K103.2, K103.3, K103.4, K103.5, K103.6, K103.7, K103.8, K103.9, K103.10, K103.11, K103.12, K103.13, K103.14, K103.15, K103.16, K103.17, K103.18, K103.19, K103.20, K103.21, K103.22, K103.23, K103.24, K103.25, K103.26, K103.27, K103.28, K103.29, K104.1, K104.2, K104.3, K104.4, K104.5, K104.6, K104.7, K104.8, K104.9, K104.10, K104.11, K104.12, K104.13, K104.14, K104.15, K104.16, K104.17, K104.18, K104.19, K104.20, K104.21, K104.22, K104.23, K104.24, K104.25, K104.26, K104.27, K104.28, K104.29, K105.1, K105.2, K105.3, K105.4, K105.5, K105.6, K105.7, K105.8, K105.9, K105.10, K105.11, K105.12, K105.13, K105.14, K105.15, K105.16, K105.17, K105.18, K105.19, K105.20, K105.21, K105.22, K105.23, K105.24, K105.25, K105.26, K105.27, K105.28, K105.29, K106.1, K106.2, K106.3, K106.4, K106.5, K106.6, K106.7, K106.8, K106.9, K106.10, K106.11, K106.12, K106.13, K106.14, K106.15, K106.16, K106.17, K106.18, K106.19, K106.20, K106.21, K106.22, K106.23, K106.24, K106.25, K106.26, K106.27, K106.28, K106.29, K107.1, K107.2, K107.3, K107.4, K107.5, K107.6, K107.7, K107.8, K107.9, K107.10, K107.11, K107.12, K107.13, K107.14, K107.15, K107.16, K107.17, K107.18, K107.19, K107.20, K107.21, K107.22, K107.23, K107.24, K107.25, K107.26, K107.27, K107.28, K107.29, K108.1, K108.2, K108.3, K108.4, K108.5, K108.6, K108.7, K108.8, K108.9, K108.10, K108.11, K108.12, K108.13, K108.14, K108.15, K108.16, K108.17, K108.18, K108.19, K108.20, K108.21, K108.22, K108.23, K108.24, K108.25, K108.26, K108.27, K108.28, K108.29, K109.1, K109.2, K109.3, K109.4, K109.5, K109.6, K109.7, K109.8, K109.9, K109.10, K109.11, K109.12, K109.13, K109.14, K109.15, K109.16, K109.17, K109.18, K109.19, K109.20, K109.21, K109.22, K109.23, K109.24, K109.25, K109.26, K109.27, K109.28, K109.29, K110.1, K110.2, K110.3, K110.4, K110.5, K110.6, K110.7, K110.8, K110.9, K110.10, K110.11, K110.12, K110.13, K110.14, K110.15, K110.16, K110.17, K110.18, K110.19, K110.20, K110.21, K110.22, K110.23, K110.24, K110.25, K110.26, K110.27, K110.28, K110.29, K111.1, K111.2, K111.3, K111.4, K111.5, K111.6, K111.7, K111.8, K111.9, K111.10, K111.11, K111.12, K111.13, K111.14, K111.15, K111.16, K111.17, K111.18, K111.19, K111.20, K111.21, K111.22, K111.23, K111.24, K111.25, K111.26, K111.27, K111.28, K111.29, K112.1, K112.2, K112.3, K112.4, K112.5, K112.6, K112.7, K112.8, K112.9, K112.10, K112.11, K112.12, K112.13, K112.14, K112.15, K112.16, K112.17, K112.18, K112.19, K112.20, K112.21, K112.22, K112.23, K112.24, K112.25, K112.26, K112.27, K112.28, K112.29, K113.1, K113.2, K113.3, K113.4, K113.5, K113.6, K113.7, K113.8, K113.9, K113.10, K113.11, K113.12, K113.13, K113.14, K113.15, K113.16, K113.17, K113.18, K113.19, K113.20, K113.21, K113.22, K113.23, K113.24, K113.25, K113.26, K113.27, K113.28, K113.29, K114.1, K114.2, K114.3, K114.4, K114.5, K114.6, K114.7, K114.8, K114.9, K114.10, K114.11, K114.12, K114.13, K114.14, K114.15, K114.16, k114.17, K114.18, K114.19, K114.20, K114.21, K114.22, K114.23, K114.24, K114.25, K114.26, K114.27, K114.28, K114.29, K115.1, K115.2, K115.3, K115.4, K115.5, K115.6, K115.7, K115.8, K115.9, K115.10, K115.11, K115.12, K115.13, K115.14, K115.15, K115.16, K115.17, K115.18, K115.19, K115.20, K115.21, K115.22, K115.23, K115.24, K115.25, K115.26, K115.27, K115.28, K115.29, K116.1, K116.2, K116.3, K116.4, K116.5, K116.6, K116.7, K116.8, K116.9, K116.10, K116.11, K116.12, K116.13, K116.14, K116.15, K116.16, K116.17, K116.18, K116.19, K116.20, K116.21, K116.22, K116.23, K116.24, K116.25, K116.26, K116.27, K116.28, K116.29, K117.1, K117.2, K117.3, K117.4, K117.5, K117.6, K117.7, K117.8, K117.9, K117.10, K117.11, K117.12, K117.13, K117.14, K117.15, K117.16, K117.17, K117.18, K117.19, K117.20, K117.21, K117.22, K117.23, K117.24, K117.25, K117.26, K117.27, K117.28, K117.29, K118.1, K118.2, K118.3, K118.4, K118.5, K118.6, K118.7, K118.8, K118.9, K118.10, K118.11, K118.12, K118.13, K118.14, K118.15, K118.16, K118.17, K118.18, K118.19, K118.20, K118.21, K118.22, K118.23, K118.24, K118.25, K118.26, K118.27, K118.28, K118.29, K119.1, K119.2, K119.3, K119.4, K119.5, K119.6, K119.7, K119.8, K119.9, K119.10, K119.11, K119.12, K119.13, K119.14, K119.15, |

TABLE 3-continued

| Binary herbicide combinations of the active compounds (A) and (B) |
|---|
| K119.16, K119.17, K119.18, K119.19, K119.20, K119.21, K119.22, K119.23, K119.24, K119.25, K119.26, K119.27, K119.28, K119.29, K120.1, K120.2, K120.3, K120.4, K120.5, K120.6, K120.7, K120.8, K120.9, K120.10, K120.11, K120.12, K120.13, K120.14, K120.15, K120.16, K120.17, K120.18, K120.19, K120.20, K120.21, K120.22, K120.23, K120.24, K120.25, K120.26, K120.27, K120.28, K120.29, K121.1, K121.2, K121.3, K121.4, K121.5, K121.6, K121.7, K121.8, K121.9, K121.10, K121.11, K121.12, K121.13, K121.14, K121.15, K121.16, K121.17, K121.18, K121.19, K121.20, K121.21, K121.22, K121.23, K121.24, K121.25, K121.26, K121.27, K121.28, K121.29, K122.1, K122.2, K122.3, K122.4, K122.5, K122.6, K122.7, K122.8, K122.9, K122.10, K122.11, K122.12, K122.13, K122.14, K122.15, K122.16, K122.17, K122.18, K122.19, K122.20, K122.21, K122.22, K122.23, K122.24, K122.25, K122.26, K122.27, K122.28, K122.29, K123.1, K123.2, K123.3, K123.4, K123.5, K123.6, K123.7, K123.8, K123.9, K123.10, K123.11, K123.12, K123.13, K123.14, K123.15, K123.16, K123.17, K123.18, K123.19, K123.20, K123.21, K123.22, K123.23, K123.24, K123.25, K123.26, K123.27, K123.28, K123.29, K124.1, K124.2, K124.3, K124.4, K124.5, K124.6, K124.7, K124.8, K124.9, K124.10, K124.11, K124.12, K124.13, K124.14, K124.15, K124.16, K124.17, K124.18, K124.19, K124.20, K124.21, K124.22, K124.23, K124.24, K124.25, K124.26, K124.27, K124.28, K124.29, K125.1, K125.2, K125.3, K125.4, K125.5, K125.6, K125.7, K125.8, K125.9, K125.10, K125.11, K125.12, K125.13, K125.14, K125.15, K125.16, K125.17, K125.18, K125.19, K125.20, K125.21, K125.22, K125.23, K125.24, K125.25, K125.26, K125.27, K125.28, K125.29, K126.1, K126.2, K126.3, K126.4, K126.5, K126.6, K126.7, K126.8, K126.9, K126.10, K126.11, K126.12, K126.13, K126.14, K126.15, K126.16, K126.17, K126.18, K126.19, K126.20, K126.21, K126.22, K126.23, K126.24, K126.25, K126.26, K126.27, K126.28, K126.29, K127.1, K127.2, K127.3, K127.4, K127.5, K127.6, K127.7, K127.8, K127.9, K127.10, K127.11, K127.12, K127.13, K127.14, K127.15, K127.16, K127.17, K127.18, K127.19, K127.20, K127.21, K127.22, K127.23, K127.24, K127.25, K127.26, K127.27, K127.28, K127.29. |

Abbreviations for Table 3:

1, See explanation prior to Table 2 for the abbreviation "Ka.b" and the codes "a" and "b"

2, Example: in the short notation of Table 3, the combination of the herbicides (A5) and (B2.3.1) is thus stated as K5.20.

From the binary combinations, preference is given to those comprising preferred compounds (A) and (B).

Preference is also given to herbicide combinations of one or more compounds (A) with one or more compounds of group (B1) or (B2) or (B3), i.e. mixtures of the binary combinations according to Table 3, particularly mixtures of preferred binary combinations.

Preference is furthermore given to combinations of one or more compounds (A) with one or more compounds (B) according to the scheme:

(A)+(B1)+(B2), (A)+(B1)+(B3), (A)+(B2)+(B3) or (A)+(B1)+(B2)+(B3).

The combinations according to the invention can furthermore be used together with other active compounds, for example from the group of the herbicides, safeners, fungicides, insecticides and plant growth regulators, or from the group of the formulation auxiliaries and additives customary in crop protection.

Additives are, for example, fertilizers and colorants. Of particular importance here are combinations to which one or more further active compounds of a different structure or safeners [active compounds (C)] are added, such as, for example, according to the scheme (A)+(B1)+(C), (A)+(B2)+(C), (A)+(B3)+(C), (A)+(B1)+(B2)+(C), (A)+(B1)+(B3)+(C), (A)+(B2)+(B3)+(C) or (A)+(B1)+(B2)+(B3)+(C).

For combinations of the last-mentioned type with three or more active compounds, the preferred conditions illustrated below in particular for two-compound combinations according to the invention primarily also apply if they comprise the two-compound combinations according to the invention, and with respect to the two-compound combination in question.

In some cases, even combinations of different active compounds from the group (A) are synergistic, so that, based on these two-compound combinations, particularly favorable three-compound combinations with additional synergistic effects are possible.

Preference is given to combinations of active compounds (A) and (B) suitable for non-selective application or application in plantation crops.

Particular preference is given to combinations of active compounds (A) with active compounds (B) from the group consisting of:

(B1.1.2) thiencarbazone-methyl, (B1.2.1) tembotrione, (B1.3) SYN-523, (B1.4.1) pyroxsulam, (B1.5.1) penoxsulam, (B1.6.1) SYN-449, (B2.1.1) pyrasulfotole, (B2.2.2) trifloxysulfuron sodium salt, (B2.3.1) saflufenacil, (B2.4.1) aminopyralid, (B2.5) ethofumesate, (B2.6) aminocyclopyrachlor and its salts and esters, in particular (B2.6.1) aminocyclopyrachlor, and (B3.1) pyroxasulfone.

Particular preference is given here to the combinations of active compounds (A) with active compounds (B) from the group consisting of:

(B1.1.2) thiencarbazone-methyl, (B1.2.1) tembotrione, (B2.1.1) pyrasulfotole and (B2.5) ethofumesate.

Preference is likewise given to multiple combinations according to the scheme below:

(A)+(B1.1.2)+(B1.2.1), (A)+(B1.1.2)+(B1.3), (A)+(B1.1.2)+(B1.4.1), (A)+(B1.1.2)+(B1.5.1), (A)+(B1.1.2)+(B1.6.1), (A)+(B1.1.2)+(B2.1.1), (A)+(B1.1.2)+(B2.2.2), (A)+(B1.1.2)+(B2.3.1), (A)+(B1.1.2)+(B2.4.1), (A)+(B1.1.2)+(B2.5), (A)+(B1.1.2)+(B2.6.1), (A)+(B1.1.2)+(B2.6.2), (A)+(B1.1.2)+(B2.6.4), (A)+(B1.1.2)+(B3.1), (A)+(B1.2.1)+(B1.3), (A)+(B1.2.1)+(B1.4.1), (A)+(B1.2.1)+(B1.5.1), (A)+(B1.2.1)+(B1.6.1), (A)+(B1.2.1)+(B2.1.1), (A)+(B1.2.1)+(B2.2.2), (A)+(B1.2.1)+(B2.3.1), (A)+(B1.2.1)+(B2.4.1), (A)+(B1.2.1)+(B2.5), (A)+(B1.2.1)+(B2.6.1), (A)+(B1.2.1)+(B2.6.2), (A)+(B1.2.1)+(B2.6.4), (A)+(B1.2.1)+(B3.1), (A)+(B1.3)+(B1.4.1), (A)+(B1.3)+(B1.5.1), (A)+(B1.3)+(B1.6.1), (A)+(B1.3)+(B2.1.1), (A)+(B1.3)+(B2.2.2), (A)+(B1.3)+(B2.3.1), (A)+(B1.3)+(B2.4.1), (A)+(B1.3)+(B2.5), (A)+(B1.3)+(B2.6.1), (A)+(B1.3)+(B2.6.2), (A)+(B1.3)+(B2.6.4), (A)+(B1.3)+(B3.1), (A)+(B1.4.1)+(B1.5.1), (A)+(B1.4.1)+(B1.6.1), (A)+(B1.4.1)+(B2.1.1), (A)+(B1.4.1)+(B2.2.2), (A)+(B1.4.1)+(B2.3.1), (A)+(B1.4.1)+(B2.4.1), (A)+(B1.4.1)+(B2.5), (A)+(B1.4.1)+(B2.6.1), (A)+(B1.4.1)+(B2.6.2), (A)+(B1.4.1)+(B2.6.4), (A)+(B1.4.1)+(B3.1), (A)+(B1.5.1)+(B1.6.1), (A)+(B1.5.1)+(B2.1.1), (A)+(B1.5.1)+(B2.2.2), (A)+(B1.5.1)+(B2.3.1), (A)+(B1.5.1)+(B2.4.1), (A)+(B1.5.1)+(B2.5), (A)+(B1.5.1)+(B2.6.1), (A)+(B1.5.1)+(B2.6.2), (A)+(B1.5.1)+(B2.6.4), (A)+(B1.5.1)+(B3.1), (A)+(B1.6.1)+(B2.1.1), (A)+(B1.6.1)+(B2.2.2), (A)+(B1.6.1)+(B2.3.1), (A)+(B1.6.1)+(B2.4.1), (A)+(B1.6.1)+(B2.5), (A)+(B1.6.1)+(B2.6.1), (A)+(B1.6.1)+(B2.6.2), (A)+(B1.6.1)+(B2.6.4), (A)+(B1.6.1)+(B3.1), (A)+(B2.1.1)+(B2.2.2), (A)+(B2.1.1)+(B2.3.1), (A)+(B2.1.1)+(B2.4.1), (A)+(B2.1.1)+(B2.5), (A)+(B2.1.1)+(B2.6.1), (A)+(B2.1.1)+(B2.6.2), (A)+(B2.1.1)+(B2.6.4), (A)+(B2.1.1)+(B3.1), (A)+(B2.2.2)+(B2.3.1), (A)+(B2.2.2)+(B2.4.1), (A)+(B2.2.2)+(B2.5), (A)+(B2.2.2)+(B2.6.1), (A)+(B2.2.2)+(B2.6.2), (A)+(B2.2.2)+(B2.6.4), (A)+(B2.2.2)+(B3.1), (A)+(B2.3.1)+(B2.4.1), (A)+(B2.3.1)+(B2.5), (A)+(B2.3.1)+(B2.6.1), (A)+(B2.3.1)+(B2.6.2), (A)+(B2.3.1)+(B2.6.4), (A)+(B2.3.1)+(B3.1), (A)+(B2.4.1)+(B2.5), (A)+(B2.4.1)+(B2.6.1), (A)+(B2.4.1)+(B2.6.2), (A)+(B2.4.1)+(B2.6.4), (A)+(B2.4.1)+(B3.1), (A)+(B2.5)+(B2.6.1), (A)+(B2.5)+(B2.6.2), (A)+(B2.5)+(B2.6.4), (A)+(B2.5)+(B3.1).

(A)+(B2.6.1)+(B2.6.2), (A)+(B2.6.1)+(B2.6.4), (A)+(B2.6.1)+(B3.1), (A)+(B2.6.2)+(B2.6.4), (A)+(B2.6.2)+(B3.1) and (A)+(B2.6.4)+(B3.1).

In this case, particular preference is given to the combinations in which (A) is one of the compounds according to Table 1.

The herbicide combinations according to the invention can also be combined with further herbicides and plant growth regulators, for example to complete the activity spectrum. Suitable combination partners for the compounds according to the invention in mixed formulations or in the tank mix are, for example, known active compounds whose action is based on an inhibition of, for example, acetolactate synthase, acetyl-CoA carboxylase, cellulose synthase, enolpyruvylshikimate 3-phosphate synthase, glutamine synthetase, p-hydroxyphenylpyruvate dioxygenase, phytoendesaturase, photosystem I, photosystem II, protoporphyrinogen oxidase, as known, for example, from Weed Research 26 (1986) 441-445 or "The Pesticide Manual", 14th Edition, The British Crop Protection Council and the Royal Soc. of Chemistry, 2006, the corresponding "e-Pesticide Manual Version 4 (2006)" and literature cited therein. Further trade names and "common names" are listed in the "Compendium of Pesticide Common Names" (searchable on the Internet under http://www.alanwood.net/pesticides).

The following active compounds, for example, may be mentioned as known herbicides which can be combined with the compounds according to the invention (note: the compounds are referred to either by the "common name" according to the International Organization for Standardization (ISO) or by the chemical name, if appropriate together with a customary code number) and include in each case all use forms, such as acids, salts, esters and isomers, such as stereoisomers and optical isomers. One and in some cases a plurality of application forms is/are mentioned:

2,4-D, acetochlor, acifluorfen, acifluorfen-sodium, aclonifen, alachlor, alloxydim, alloxydim-sodium, ametryn, amicarbazone, amidosulfuron, amitrole, anilofos, asulam, atrazine, azafenidin, azimsulfuron, beflubutamid, benazolin, benazolin-ethyl, benfuresate, bensulfuron-methyl, bentazone, benzfendizone, benzobicyclon, benzofenap, bifenox, bilanafos, bispyribac-sodium, bromacil, bromobutide, bromofenoxim, bromoxynil, butachlor, butafenacil, butenachlor, butralin, butroxydim, butylate, cafenstrole, carbetamide, carfentrazone-ethyl, chlomethoxyfen, chloridazon, chlorimuron-ethyl, chlornitrofen, chlorotoluron, chlorsulfuron, cinidon-ethyl, cinmethylin, cinosulfuron, clefoxydim, clethodim, clodinafop-propargyl, clomazone, clomeprop, clopyralid, cloransulam-methyl, cumyluron, cyanazine, cyclosulfamuron, cycloxydim, cyhalofop-butyl, desmedipham, dicamba, dichlobenil, dichlorprop, dichlorprop-P, diclofop-methyl, diclosulam, difenzoquat, diflufenican, diflufenzopyr, dikegulac-sodium, dimefuron, dimepiperate, dimethachlor, dimethametryn, dimethenamid, Triaziflam, diquat-dibromide, dithiopyr, diuron, dymron, EPTC, esprocarb, ethalfluralin, ethametsulfuron-methyl, ethoxyfen, ethoxysulfuron, etobenzanid, fenoxaprop-ethyl, fenoxaprop-P-ethyl, fentrazamide, flamprop-M-isopropyl, flamprop-M-methyl, flazasulfuron, florasulam, fluazifop, fluazifop-butyl, fluazifop-P-butyl, fluazolate, flucarbazone-sodium, flucetosulfuron, fluchloralin, flufenacet, flufenpyr, flumetsulam, flumiclorac-pentyl, flumioxazin, fluometuron, fluorochloridone, fluoroglycofen-ethyl, flupoxam, flupyrsulfuron-methyl-sodium, fluridone, fluoroxypyr, fluoroxypyr-butoxypropyl, fluoroxypyr-meptyl, flurprimidol, flurtamone, fluthiacet-methyl, fomesafen, foramsulfuron, glufosinate, glufosinate-ammonium, glyphosate, halosulfuron-methyl, haloxyfop, haloxyfop-ethoxyethyl, haloxyfop-methyl, haloxyfop-P-methyl, hexazinone, imazamethabenz-methyl, imazamox, imazapic, imazapyr, imazaquin, imazethapyr, imazosulfuron, indanofan, iodosulfuron-methyl-sodium, ioxynil, isoproturon, isouron, isoxaben, isoxachlortole, isoxaflutole, ketospiradox, lactofen, lenacil, linuron, MCPA, mecoprop, mecoprop-P, mefenacet, mesosulfuron-methyl, mesotrione, metamifop, metamitron, metazachlor, methabenzthiazuron, methyldymron, metobromuron, metolachlor, metosulam, metoxuron, metribuzin, metsulfuron-methyl, molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, pethoxamid, phenmedipham, picloram, picolinafen, pinoxaden, piperophos, pretilachlor, primisulfuron-methyl, profluazol, profoxydim, prometryn, propachlor, propanil, propaquizafop, propisochlor, propoxycarbazone-sodium, propyzamide, prosulfocarb, prosulfuron, pyraclonil, pyraflufen-ethyl, pyrazolate, pyrazosulfuron-ethyl, pyrazoxyfen, pyribenzoxim, pyributicarb, pyridafol, pyridate, pyriftalid, pyriminobac-methyl, pyrithiobac-sodium, quinclorac, quinmerac, quinoclamine, quizalofop-ethyl, quizalofop-P-ethyl, quizalofop-P-tefuryl, rimsulfuron, sethoxydim, simazine, simetryn, S-metolachlor, sulcotrione, sulfentrazone, sulfometuron-methyl, sulfosate, sulfosulfuron, tebuthiuron, tepraloxydim, terbuthylazine, terbutryn, thenylchlor, thiazopyr, thifensulfuron-methyl, thiobencarb, tiocarbazil, tralkoxydim, triallate, triasulfuron, tribenuron-methyl, triclopyr, tridiphane, trifloxysulfuron, trifluralin, triflusulfuron-methyl, tritosulfuron, WL 110547, i.e. 5-phenoxy-1-[3-(trifluoromethyl) phenyl]-1H-tetrazole; HOK-201, HOK-202, UBH-509; D-489; LS 82-556; KPP-300; NC-324; NC-330; KH-218; DPX-N8189; SC-0774; TH-547, DOWCO-535; DK-8910; V-53482; PP-600; MBH-001; KIH-9201; ET-751; KIH-6127; KIH-2023 and KIH5996. If the respective name (common name) includes more than one form of the active compound, the name preferably defines the commercially available form.

Each of the further active compounds mentioned (=active compounds (C*), (C1*), (C2*) etc.) can then preferably be combined with one of the two-compound combinations K1.1 to K127.29, according to the scheme (A)+(B)+(C*) or else according to scheme (A)+(B)+(C1*)+(C2*) etc. This also includes those multiple combinations in which the compounds (C*), (C1*) or (C2*) are selected from the group of the compounds (B), but are not identical to the compound (B) present in respective two-compound combinations.

The stated amounts are application rates (g of AS/ha=gram of active compound per hectare) and thus also define the ratios in a coformulation, a pre-mix, a tank mix or a sequential application of the combined active compounds.

The combinations can be applied both by the pre-emergence method and by the post-emergence method. This applies both to pre- and post-emergence with respect to the harmful plants and, in the selective control of harmful plants, to the pre- or post-emergence of the crop plants. Mixed forms are also possible, for example after the emergence of the crop plants the control of the harmful plants at their pre- or post-emergence stage.

Other suitable combination partners include crop plant-protecting active compounds (called "safeners" or "antidotes") which are able to prevent or reduce phytotoxic effects of the herbicides in crop plants.

Suitable safeners for the above-mentioned herbicidally active compounds (A) or combinations of herbicides (A) and (B) or generally for the combinations according to the invention are, for example, the following groups of compounds; the compounds are in each case referred to by the respective "common name" or code numbers with structure (references for the common names: see the "Pesticide Manual" mentioned above or "Compendium of Pesticide Common Names"): benoxacor, cloquintocet(-mexyl), cyometrinil, cyprosulfamide, dichlormid, dicyclonon, dietholate, disulfoton (=O,O-diethyl S-2-ethylthioethyl phosphordithioate), fenchlorazole(-ethyl), fenclorim, flurazole, fluxofenim, furilazole, isoxadifen(-ethyl). mefenpyr(-diethyl), mephenate, naphthalic anhydride, oxabetrinil, "R-29148" (=3-dichloroacetyl-2,2,5-trimethyl-1,3-oxazolidine), "R-28725" (=3-dichloroacetyl-2.2,-dimethyl-1,3-oxazolidine), "PPG-1292" (=N-allyl-N-[(1,3-dioxolan-2-yl)methyl]-dichloroacetamide), "DKA-24" (=N-allyl-N-[(allylaminocarbonyl)methyl]-dichloroacetamide), "AD-67" or "MON 4660" (=3-dichloroacetyl-1-oxa-3-aza-spiro[4.5]decane), "TI-35" (=1-dichloroacetylazepane), "dimepiperate" or "MY-93" (=S-1-methyl-1-phenylethyl piperidine-1-thiocarboxylate), "daimuron" or "SK 23" (=1-(1-methyl-1-phenylethyl)-3-p-tolylurea), "cumyluron"="JC-940" (=3-(2-chlorophenylmethyl)-1-(1-methyl-1-phenylethyl)urea), "methoxyphenone", or "NK 049" (=3,3'-dimethyl-4-methoxybenzophenone), "CSB" (=1-bromo-4-(chloromethylsulfonyl)benzene), "CL-304415" (=4-carboxy-3,4-dihydro-2H-1-benzopyran-4-acetic acid; CAS-Regno: 31541-57-8), "MG-191" (=2-dichloromethyl-2-methyl-1,3-dioxolane), "MG-838" (=2-propenyl 1-oxa-4-azaspiro[4.5]decane-4-carbodithioate; CAS-Regno: 133993-74-5), methyl(diphenylmethoxy)acetate (CAS-Regno: 41858-19-9 from WO-A-1998/38856), methyl [(3-oxo-1H-2-benzothiopyran-4(3H)-ylidene)methoxy]acetate (CAS-Regno: 205121-04-6 from WO-A-1998/13361), 1,2-dihydro-4-hydroxy-1-methyl-3-(5-tetrazolylcarbonyl)-2-quinolone (CAS-Regno: 95855-00-8 from WO-A-1999/000020).

From among the safeners mentioned, benoxacor, cloquintocet(-mexyl), cyometrinil, cyprosulfamide, dichlormid, fenchlorazole(-ethyl), fenclorim, flurazole, fluxofenim, furilazole, isoxadifen(-ethyl), mefenpyr (-diethyl), naphthalic anhydride, oxabetrinil, "AD-67" (="MON 4660"=3-dichloroacetyl-1-oxa-3-azaspiro[4,5] decane), "TI-35" (=1-dichloroacetylazepane), dimepiperate, daimuron, cumyluron, are of particular interest.

Some of the safeners have already been mentioned as herbicides and, accordingly, in addition to the herbicidal action on harmful plants, also have a protective action on the crop plants.

Each of the safeners mentioned can be combined as further active compound (C) preferably with one of the two-compound combinations K1.1 to K127.29 mentioned which comprises a compound (B) having a structure different from the compound (C) in question, according to the scheme (A)+(B)+(C).

The herbicide combinations according to the invention may comprise further components, for example other active compounds against harmful organisms such as harmful plants, plant-damaging animals or plant-damaging fungi, in particular active compounds from the group of the herbicides, fungicides, insecticides, acaricides, nematicides, miticides, and related substances.

Fungicidally active compounds which can be used in combination with the herbicide combinations according to the invention are preferably commercially available active compounds, for example (analogously to the herbicides, the compounds are generally referred to by their common names):

2-phenylphenol; 8-hydroxyquinoline sulfate; acibenzolar-S-methyl; actinovate; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; binapacryl; biphenyl; bitertanol; blasticidin-S; boscalid; bromuconazole; bupirimate; buthiobate; butylamine; calcium polysulfide; capsimycin; captafol; captan; carbendazim; carboxin; carpropamid; carvone; chinomethionat; chlobenthiazone; chlorfenazole; chloroneb; chlorothalonil; chlozolinate; cis-1-(4-chlorophenyl)-2-(1H-1,2,4-triazol-1-yl)cycloheptanol; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-AI; fosetyl-sodium; fuberidazole; furalaxyl; furametpyr; furcarbanil; furmecyclox; guazatine; hexachlorobenzene; hexaconazole; hymexazol; imazalil; imibenconazole; iminoctadine triacetate; iminoctadine tris (albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; methyl 1-(2,3-dihydro-2,2-dimethyl-1H-inden-1-yl)-1H-imidazole-5-carboxylate; methyl 2-[[[cyclopropyl[(4-methoxyphenyl)imino]methyl]thio]methyl]-.alpha.-(methoxymethylene) benzeneacetate; methyl 2-[2-[3-(4-chlorophenyl)-1-methyl-allylideneaminooxymethyl] phenyl]-3-methoxyacrylate; metiram; metominostrobin; metrafenone; metsulfovax; mildiomycin; monopotassium carbonate; myclobutanil; myclozolin; nabam, N-(3-ethyl-3,5,5-trimethylcyclohexyl)-3-formylamino-2-hydroxybenzamide; N-(6-methoxy-3-pyridinyl)cyclopropanecarboxamide; N-butyl-8-(1,1-dimethylethyl)-1-oxaspiro[4.5] decan-3-amine; natamycin; nitrothal-isopropyl; noviflumuron; nuarimol; ofurace; orysastrobin; oxadixyl; oxolinic acid; oxpoconazole; oxycarboxin; oxyfenthiin; paclobutrazol; pefurazoate: penconazole; pencycuron; penthiopyrad; phosdiphen; phthalide; picobenzamid; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolnitrine; quinconazole; quinoxyfen; quintozene; silthiofam; simeconazole; sodium tetrathiocarbonate; spiroxamine; sulfur; tebuconazole; tecloftalam; tecnazene; tetcyclacis; tetraconazole; thiabendazole; thicyofen; thifluzamide; thiophanate-methyl; thiram; tiadinil; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)—N-[2-[4-[[3-(4-chlorophenyl)-2-propynyl]oxy]-3-methoxyphenyl]ethyl]-3-methyl-2-[(methylsulfonyl) amino]-butanamide; 1-(1-naphthalenyl)-1H-pyrrole-2,5-dione; 2,3,5,6-tetrachloro-4-(methylsulfonyl)pyridine; 2,4-dihydro-5-methoxy-2-methyl-4-[[[[1-[3-(trifluoromethyl)phenyl]ethylidene]amino]oxy]methyl]phenyl]-3H-1,2,3-triazol-3-one; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; 3-[(3-bromo-6-fluoro-2-methyl-1H-indol-1-yl)sulfonyl]-N,N-dimethyl-1H-1,2,4-triazole-1-sulfonamide; copper salts and copper preparations, such as Bordeaux mixture; copper hydroxide; copper naphthenate; copper oxychloride; copper sulfate; cufraneb; copper(I) oxide; mancopper; oxine-copper.

Preferred fungicides are selected from the group consisting of benalaxyl, bitertanol, bromuconazole, captafol, carbendazim, carpropamid, cyazofamid, cyproconazole, diethofencarb, edifenphos, fenpropimorph, fentine, fluquinconazole, fosetyl, fluoroimide, folpet, iminoctadine, iprodionem, iprovalicarb, kasugamycin, maneb, nabam, pencycuron, prochloraz, propamocarb, propineb, pyrimethanil, spiroxamine, quintozene, tebuconazole, tolylfluanid, triadimefon, triadimenol, trifloxystrobin, zineb.

Insecticidal, acaricidal, nematicidal, miticidal and related active compounds are, for example (analogously to the herbicides and fungicides, the compounds are, if possible, referred to by their common names):

alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion, acrinathrin, allethrin (d-cis-trans, d-trans), beta-cyfluthrin, bifenthrin, bioallethrin, bioallethrin-S-cyclopentyl-isomer, bioethanomethrin, biopermethrin, bioresmethrin, chlovaporthrin, cis-cypermethrin cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (-1R-isomer), tralomethrin, transfluthrin, ZXI 8901, pyrethrins (pyrethrum), DDT, indoxacarb, acetamiprid, clothianidin, dinotefuran, imidacloprid, nitenpyram, nithiazine, thiacloprid, thiamethoxam, nicotine, bensultap, cartap, camphechlor, chlordane, endosulfan, gamma-HCH, HCH, heptachlor, lindane, methoxychlor spinosad, acetoprole, ethiprole, fipronil, vaniliprole, avermectin, emamectin, emamectin-benzoate, ivermectin, milbemycin, diofenolan, epofenonane, fenoxycarb, hydroprene, kinoprene, methoprene, pyriproxifen, triprene, chromafenozide, halofenozide, methoxyfenozide, tebufenozide, bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron, buprofezin, cyromazine, diafenthiuron, azocyclotin, cyhexatin, fenbutatin-oxide, chlorfenapyr, binapacyrl, dinobuton, dinocap, DNOC, fenazaquin, fenpyroximate, pyrimidifen, pyridaben, tebufenpyrad, tolfenpyrad, hydramethylnon, dicofol, rotenone, acequinocyl, fluacrypyrim, Bacillus thuringiensis strains, spirodiclofen, spiromesifen, 3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester, CAS-Reg.-No.: 382608-10-8) and carbonic acid, cis-3-(2,5-dimethylphenyl)-8-methoxy-2-oxo-1-azaspiro[4.5]dec-3-en-4-yl ethyl ester (CAS-Reg.-No.: 203313-25-1), flonicamid, amitraz, propargite, N2-[1,1-dimethyl-2-(methylsulfonyl)ethyl]-3-iodo-N1-[2-methyl-4-[1,2,2,2-tetrafluoro-1-(trifluoromethyl)ethyl]phenyl]-1,2-benzenedicarboxamide (CAS-Reg.-No.: 272451-65-7), thiocyclam hydrogen oxalate, thiosultap-sodium, azadirachtin, Bacillus spec., Beauveria spec., codlemone, Metarrhizium spec., Paecilomyces spec., thuringiensin, Verticillium spec., aluminum phosphide, methyl bromide, sulfuryl fluoride, cryolite, flonicamid, pymetrozine, clofentezine, etoxazole, hexythiazox, amidoflumet, benclothiaz, benzoximate, bifenazate, bromopropylate, buprofezin, chinomethionat, chlordimeform, chlorobenzilate, chloropicrin, clothiazoben, cycloprene, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin.

Insecticides which may preferably be used together with the herbicides are, for example, the following:

acetamiprid, acrinathrin, aldicarb, amitraz, acinphos-methyl, cyfluthrin, carbaryl, cypermethrin, deltamethrin, endosulfan, ethoprophos, fenamiphos, fenthion, fipronil, imidacloprid, methamidophos, methiocarb, niclosamide, oxydemeton-methyl, prothiophos, silafluofen, thiacloprid, thiodicarb, tralomethrin, triazophos, trichlorfon, triflumuron, terbufos, fonofos, phorate, chlorpyriphos, carbofuran, tefluthrin.

The active compound combinations according to the invention are suitable for controlling a broad spectrum of weeds on non-crop land, on paths, rail tracks, industrial terrain ("industrial weed control") or in plantation crops, such as moderate, subtropical and tropical climates or geographies. Examples of plantation crops are oil palms, nuts (for example almonds, hazelnuts, walnuts, macadamia), coconut, berries, oil palms, rubber tree, citrus (for example orange, lemon, mandarin), bananas, pineapples, cotton, sugarcane, tea, coffee, cacao and the like. They are also suitable for use in the cultivation of fruits (for example pome fruit, such as apple, pear, cherry, mango, kiwi) and viticulture. The compositions can also be used for preparing the soil for sowing ("burn-down" "no-till" or "zero-till" method) or for treatment after harvest ("chemical fallow"). Potential applications of the active compound combinations extend to weed control in tree crops, for example young Christmas tree crops or eucalyptus plantations, in each case prior to planting or after transplanting (also by over-top treatment).

The compositions can also be used in selected crops of economically important crops, such as cereals (wheat, barley, rye, oats, sorghum, corn and rice), sugarbeet, sugarcane, oil seed rape, cotton, soybean, potatoes, tomatoes, peas and other varieties of vegetables. When using the active compounds (A) and (B) in crop plants such as cereals and corn, it may, depending on the crop plant, be expedient to apply a safener above certain application rates to prevent or reduce damage to the crop plant.

The herbicidally active compound combinations according to the invention in the respective use forms (=herbicidal compositions) are synergistically effective with respect to herbicide action and selectivity and have a favorable action with a view to the weed spectrum. They have excellent herbicidal activity against a broad spectrum of economically important monocotyledonous or dicotyledonous annual harmful plants. The active compounds even act efficiently on perennial harmful plants which produce shoots from rhizomes, root stocks or other perennial organs and which are difficult to control.

For use, the active compound combinations can be applied to the plants (for example harmful plants, such as monocotyledonous or dicotyledonous weeds or unwanted crop plants), the seed (for example grains, seeds or vegetative propagation organs, such as tubers or shoot parts with buds) or to the area in which the plants grow (for example the area under cultivation).

In this context, the substances can be applied before sowing (if appropriate also by incorporation into the ground), pre-emergence or post-emergence. Application by the early post-sowing pre-emergence method or by the post-emergence method of plantation crops against harmful plants which have not yet emerged or which have already emerged is preferred. The application may also be integrated into weed management systems with repeat split applications (sequence applications, sequentials).

Specifically, examples may be mentioned of some representatives of the monocotyledonous and dicotyledonous weed flora which can be controlled by the active compound combinations according to the invention, without the enumeration being a restriction to certain species.

From among the monocotyledonous weed species, for example, the compositions control Aegilops, Agropyron, Agrostis, Alopecurus, Apera, Avena, Brachicaria, Bromus, Cynodon, Dactyloctenium, Digitaria, Echinochloa, Eleocharis, Eleusine, Eragrostis, Eriochloa, Festuca, Fimbristylis, Imperata, Ischaemum, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum, Sphenoclea and Cyperus species from the annual group.

In the case of dicotyledonous weed species, the activity spectrum extends to species such as, for example, Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erodium, Erysimum, Euphorbia, Galeopsis, Galinsoga, Galium, Geranium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

If the active compound combinations according to the invention are applied to the soil surface before germination, then the weed seedlings are either prevented completely from emerging, or the weeds grow until they have reached the cotyledonous stage but then their growth stops, and, eventually, after three to four weeks have elapsed, they die completely.

If the active compounds are applied post-emergence to the green parts of the plants, growth stops after the treatment and the harmful plants remain at the growth stage of the point of time of application, or they die completely after a certain time, so that in this manner competition by the weeds, which is harmful to the crop plants, is eliminated at a very early point in time and in a sustained manner.

The herbicidal compositions according to the invention are distinguished by a rapidly commencing and long-lasting herbicidal action. As a rule, the rain fastness of the active compounds in the combinations according to the invention is advantageous. A particular advantage is that the dosages of compounds (A) and (B), which are used in the combinations and are effective, can be adjusted to such a low quantity that their soil action is optimally low. Not only does this allow them to be employed in sensitive crops in the first place, but ground water contaminations are virtually avoided. The combination according to the invention of active compounds allows the application rate of the active compounds required to be reduced considerably.

The combined use of the herbicides (A) and (B) achieves application properties which exceed what would have been expected based on the known properties of the individual herbicides for their combination. For example, for a certain species of harmful plant, the herbicidal activities exceed the expected value estimated by standard methods, for example according to Colby (see below) or other extrapolation methods.

The synergistic effects therefore allow, for example, the application rates of the individual active compounds to be reduced, a higher efficacy at the same application rate, the control of previously uncontrolled species of harmful plants (gaps), higher residual action, longer long-term action, a more rapid onset of action, an extension of the period of application and/or a reduction of the number of individual applications required and—as a result for the user—weed control systems which are more advantageous economically and ecologically.

While the combinations according to the invention have an outstanding herbicidal activity against monocotyledonous and dicotyledonous weeds, many economically important crop plants are damaged only to a minor extent, if at all, depending on the structure of the respective active compound combinations according to the invention and their application rate. Economically important crops are in this context, for example, dicotyledonous crops of the genera Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia, or monocotyledonous crops of the genera Allium, Ananas, Asparagus, Avena, Hordeum, Oryza, Panicum, Saccharum, Secale, Sorghum, Triticale, Triticum and Zea.

Some of the compositions according to the invention additionally have outstanding growth-regulatory properties in crop plants. They engage in a plant's metabolism in a regulatory fashion and can thus be employed for targeted influencing of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops, allowing lodging to be reduced or prevented completely.

On account of their herbicidal and plant growth-regulatory properties, the compositions can be employed for controlling harmful plants in crops of known plants or tolerant crop plants which are yet to be developed and are modified by conventional mutagenesis or genetically. As a rule, the transgenic plants are distinguished by particularly advantageous properties, in addition to resistances to the compositions according to the invention, for example by resistances to plant diseases or plant pathogens, such as certain insects or microorganisms such as fungi, bacteria or viruses. Other particular properties relate, for example, to the harvested material with respect to quantity, quality, storability, composition and specific constituents. Thus, transgenic plants with an increased starch content or in which the quality of the starch is altered, or those having a different fatty acid composition of the harvested material, are known. Further particular properties can be found in a tolerance or resistance to abiotic stress factors, for example, heat, cold, drought, salt and ultraviolet light.

Preferably, the active compound combinations according to the invention can be used as herbicides in crops of useful plants which are resistant to or have been made genetically resistant to the phytotoxic actions of the herbicides.

Traditional ways of generating novel plants which have modified characteristics in comparison with existing plants consist, for example, in traditional breeding methods and the generation of mutants. Alternatively, novel plants with modified characteristics can be generated using recombinant procedures (see, for example, EP-A-0221044, EP-A-0131624). For example, a number of cases have been described of

- recombinant modifications of crop plants for the purpose of modifying the starch synthesized in the plants (for example WO 92/11376, WO 92/14827, WO 91/19806),
- transgenic crop plants which are resistant to other herbicides, for example to sulfonylureas (EP-A-0257993, U.S. Pat. No. 5,013,659),
- transgenic crop plants, with the capability of producing Bacillus thuringiensis toxins (Bt toxins) which make the plants resistant to certain pests (EP-A-0142924, EP-A-0193259),
- transgenic crop plants having a modified fatty acid composition (WO 91/13972).
- genetically modified crop plants having novel constituents or secondary compounds, for example novel phytoalexins providing increased resistance to disease (EPA 309862, EPA0464461)
- genetically modified plants having reduced photorespiration, which provide higher yields and have higher stress tolerance (EPA 0305398)

transgenic crop plants producing pharmaceutically or diagnostically important proteins ("molecular pharming")

transgenic crop plants distinguished by higher yields or better quality transgenic crop plants distinguished by a combination, for example of the novel properties mentioned above ("gene stacking").

A large number of molecular-biological techniques with which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg or Christou, "Trends in Plant Science" 1 (1996) 423-431).

To carry out such recombinant manipulations, nucleic acid molecules which permit a mutagenesis or a sequence modification by recombination of DNA sequences can be introduced into plasmids. For example, it is possible with the aid of standard methods to carry out base exchanges, to remove subsequences or to add natural or synthetic sequences. Adapters or linkers may be added in order to link the DNA fragments to each other, see, for example, Sambrook et al., 1989, Molecular Cloning, A Laboratory Manual, 2nd Ed., Cold Spring Harbor Laboratory Press, Cold Spring Harbor, N.Y.; or Winnacker "Gene and Klone" [Genes and Clones], VCH Weinheim 2nd Edition 1996.

For example, plant cells with a reduced activity of a gene product can successfully be generated by expressing at least one suitable antisense RNA, a sense RNA to achieve a cosuppression effect or by expressing at least one suitably constructed ribozyme which specifically cleaves transcripts of the abovementioned gene product.

To this end, it is possible to use firstly DNA molecules which encompass all of the coding sequence of a gene product including any flanking sequences which may be present and secondly DNA molecules which only encompass parts of the coding sequence, it being necessary for these parts to be of sufficient length to cause an antisense effect in the cells. Also possible is the use of DNA sequences which have a high degree of homology with the coding sequences of a gene product which are not entirely identical thereto.

When expressing nucleic acid molecules in plants, the protein synthesized may be localized in any compartment of the plant cell. However, to achieve localization in a particular compartment, it is possible for example to link the coding region with DNA sequences which guarantee localization in a certain compartment. Sequences of this type are known to the person skilled in the art, (see, for example. Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give intact plants. In principle, the transgenic plants can be plants of any desired plant species, i.e. both monocotyledonous and dicotyledonous plants. Transgenic plants are thus obtainable which have modified properties as a result of overexpression, suppression or inhibition of homologous (=natural) genes or gene sequences, or expression of heterologous (=foreign) genes or gene sequences.

The active compound combinations according to the invention may preferably be used in transgenic crops which are tolerant or have been made tolerant to the active compounds employed.

Preferably, the active compound combinations according to the invention can also be used in transgenic crops resistant to growth substances, such as, for example, dicamba, or to herbicides inhibiting essential plant enzymes, for example acetolactate synthases (ALS), EPSP synthases, glutamine synthases (GS) or hydroxyphenylpyruvate dioxygenases (HPPD), respectively, to herbicides from the group of the sulfonylureas, the glyphosates, glufosinates or benzoylisoxazoles and analogous active compounds.

The invention therefore also provides a method for controlling unwanted vegetation, if appropriate in crops of useful plants, preferably on non-crop land or in plantation crops, wherein one or more herbicides of type (A) and one or more herbicides of type (B) are applied to the harmful plants, to parts of plants or plant seeds (seed) thereof, or to the area under cultivation.

The invention also provides the use of the novel combinations of compounds (A)+(B) for controlling harmful plants, if appropriate in crops of useful plants, preferably on non-crop land and in plantation crops.

The active compound combinations according to the invention can also be present as mixed formulations of the two components, if appropriate with further active compounds, additives and/or customary formulation auxiliaries, which are then applied in a customary manner diluted with water, or are produced as tank mixes by joint dilution of the separately formulated or partially separately formulated components with water.

The compounds (A) and (B) or their combinations can be formulated in various ways, depending on the prevailing biological and/or chemico-physical parameters. Examples of suitable formulations which are possible are: wettable powders (WP), water-soluble powders (SP), emulsifiable concentrates (EC), water-soluble concentrates, aqueous solutions (SL), emulsions (EW), such as oil-in-water and water-in-oil emulsions, sprayable solutions or emulsions, oil- or water-based dispersions, oil dispersions (OD), suspoemulsions, suspension concentrates (SC), oil-miscible solutions, capsule suspensions (CS), dusts (DP), seed-dressing products, granules for spreading and soil application, granules (GR) in the form of microgranules, wettable granules, coated granules and adsorption granules, water-dispersible granules (WG), water-soluble granules (SG), ULV formulations, microcapsules and waxes.

The invention therefore also relates to herbicidal and plant growth-regulatory compositions which comprise the active compound combinations according to the invention.

The individual formulation types are known in principle and are described, for example, in Winnacker-Küchler, "Chemische Technologie" [Chemical Engineering], Volume 7, C. Hanser Verlag Munich, 4th Ed. 1986, van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; Marsden, "Solvents Guide"; 2nd Ed., Interscience. N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologic", Volume 7, C. Hanser Verlag Munich, 4th Ed. 1986.

Based on these formulations, it is also possible to prepare combinations with other pesticidally active compounds such as other herbicides, fungicides, insecticides or other pest control agents (for example, acaricides, nematicides, molluscicides, rodenticides, aphicides, avicides, larvicides, ovicides, bactericides, virucides, etc.), and with safeners, fertilizers and/or growth regulators, for example in the form of a ready-mix or a tank mix.

Wettable powders are preparations which are uniformly dispersible in water and which, in addition to the active compound, also contain ionic and/or nonionic surfactants (wetters, dispersants), for example polyoxyethylated alkylphenols, polyoxethylated fatty alcohols, polyoxethylated fatty amines, fatty alcohol polyglycol ether sulfates, alkane-sulfonates, alkylbenzenesulfonates, sodium lignosulfonate, sodium 2,2'-dinaphthylmethane-6,6'-disulfonate, sodium dibutylnaphthalene-sulfonate or else sodium oleoylmethyltaurate, in addition to a diluent or inert substance. For preparing the wettable powders, the herbicidally active compounds are finely ground, for example in conventional apparatus such as hammer mills, blower mills and airjet mills, and simultaneously or subsequently admixed with the formulation auxiliaries.

Emulsifiable concentrates are prepared by dissolving the active compound in an organic solvent, e.g. butanol, cyclohexanone, dimethylformamide, xylene or else higher-boiling aromatics or hydrocarbons or mixtures of the organic solvents with addition of one or more surfactants of ionic and/or nonionic type (emulsifiers). Examples of emulsifiers which can be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters or such as, for example, polyoxyethylene sorbitan fatty acid esters.

Dusts are obtained by grinding the active compound with finely divided solid materials, for example talc, natural clays such as kaolin, bentonite and pyrophyllite, or diatomaceous earth.

Suspension concentrates can be water-based or oil-based. They can be prepared, for example, by wet grinding using conventional bead mills, if appropriate with the addition of surfactants, as already listed, for example, above for the other formulation types.

Emulsions, for example oil-in-water emulsions (EW), can be prepared, for example, with the aid of stirrers, colloid mills and/or static mixers using aqueous organic solvents and, if appropriate, surfactants, for example as already listed above for the other formulation types.

Granules can be prepared either by spraying the active compound onto adsorptive, granulated inert material or by applying active compound concentrates to the surface of carriers such as sand, kaolinites or granulated inert material with the aid of stickers, for example polyvinyl alcohol, sodium polyacrylate or else mineral oils. Suitable active compounds can also be granulated in the fashion which is conventional for the production of fertilizer granules, if desired as a mixture with fertilizers.

Water-dispersible granules are generally prepared by customary methods such as spray drying, fluidized-bed granulation, disk granulation, mixing with high-speed stirrers and extrusion without solid inert material.

As a rule, the agrochemical preparations comprise 0.1 to 99% by weight, in particular 0.2 to 95% by weight, of active compounds of types (A) and/or (B), the following concentrations being customary depending on the type of formulation. In wettable powders, the active compound concentration is, for example, approximately 10 to 95% by weight, the remainder to 100% by weight being composed of customary formulation constituents. In the case of emulsifiable concentrates, the active compound concentration can amount to approximately 1 to 90% by weight, preferably 5 to 80% by weight.

Formulations in the form of dusts comprise in most cases 5 to 20% by weight of active compound, and sprayable solutions comprise approximately 0.05 to 80, preferably 2 to 50% by weight of active compound.

In the case of dispersible granules, the active compound content depends partly on whether the active compound is in liquid or solid form and on the granulation auxiliaries and fillers which are being used. In the case of the water-dispersible granules, the active compound content is generally between 1 and 95% by weight, preferably between 10 and 80% by weight.

In addition, the active compound formulations mentioned comprise, if appropriate, the auxiliaries which are conventional in each case, such as stickers, wetters, dispersants, emulsifiers, penetrants, preservatives, antifreeze agents, solvents, fillers, carriers, colorants, antifoams, evaporation inhibitors, and pH and viscosity regulators.

For use, the formulations, which are present in commercially available form, are optionally diluted in the customary manner, for example using water in the case of wettable powders, emulsifiable concentrates, dispersions and water-dispersible granules. Preparations in the form of dusts, soil granules, granules for broadcasting and sprayable solutions are usually not diluted further with other inert substances prior to use.

The active compounds can be applied to the plants, parts of the plants, seeds of the plants or the area under cultivation (soil of a field), preferably to the green plants and parts of the plants and, if appropriate, additionally to the soil of the field.

One possible use is the joint application of the active compounds in the form of tank mixes, the concentrated formulations of the individual active compounds, in optical formulations, jointly being mixed with water in the tank and the resulting spray mixture being applied.

A joint herbicidal formulation of the combination according to the invention of the active compounds (A) and (B) has the advantage of being easier to apply since the quantities of the components are already presented in the correct ratio to each other. Moreover, the adjuvants in the formulation can be matched optimally to each other, whereas a tank mix of different formulations may result in undesirable combinations of adjuvants.

A. GENERAL FORMULATION EXAMPLES a) A dust is obtained by mixing 10 parts by weight of an active compound (A) or (B) or of an active compound mixture (A)+(B) (and if appropriate further active compound components) and/or salts thereof and 90 parts by weight of talc as inert material and comminuting the mixture in a hammer mill.

b) A wettable powder which is readily dispersible in water is obtained by mixing 25 parts by weight of an active compound/active compound mixture, 64 parts by weight of kaolin-containing quartz as inert material, 10 parts by weight of potassium lignosulfonate and 1 part by weight of sodium oleoylmethyltaurinate as wetter and dispersant, and grinding the mixture in a pinned-disk mill.

c) A dispersion concentrate which is readily dispersible in water is obtained by mixing 20 parts by weight of an active compound/active compound mixture with 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to 277° C.), and grinding the mixture in a ball mill to a fineness of below 5 microns.

d) An emulsifiable concentrate is obtained from 15 parts by weight of an active compound/active compound mixture, 75 parts by weight of cyclohexanone as solvent and 10 parts by weight of oxethylated nonylphenol as emulsifier.

e) Water-dispersible granules are obtained by mixing
75 parts by weight of an active compound/active compound mixture,
10 parts by weight of calcium lignosulfonate,
5 parts by weight of sodium lauryl sulfate,
3 parts by weight of polyvinyl alcohol and
7 parts by weight of kaolin,
grinding the mixture on a pinned-disk mill and granulating the powder in a fluidized bed by spraying on water as granulation liquid.

f) Water-dispersible granules are also obtained by homogenizing and precomminuting, in a colloid mill,
25 parts by weight of an active compound/active compound mixture,
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water,
subsequently grinding the mixture in a bead mill and atomizing and drying the resulting suspension in a spray tower by means of a single-substance nozzle.

B. BIOLOGICAL EXAMPLES

1. Pre-emergence Herbicidal Action

Seeds or rhizome pieces of monocotyledonous and dicotyledonous harmful plants are placed in sandy loam in pots and covered with soil. The compositions, formulated as concentrated aqueous solutions, wettable powders or emulsion concentrates, are then applied to the surface of the covering soil as an aqueous solution, suspension or emulsion at an application rate of 300 to 800l of water/ha (converted) in a variety of dosages. After the treatment, the pots are placed in a greenhouse and kept under good growth conditions for the weeds. Visual scoring of plant or emergence damage is carried out after the test plants have emerged after an experimental period of 3 to 4 weeks in comparison with untreated controls. As demonstrated by the test results, the compositions according to the invention have an outstanding pre-emergence herbicidal action against a broad spectrum of weed grasses and broad-leaf weeds.

Scoring and Assessing of the Synergistic Herbicidal Effects:

The herbicidal efficacy of the active compounds or active compound mixtures was scored visually by comparing the treated pots (soil) with untreated controls. The damage and development of all above-ground plant parts was recorded. Scoring was done on a percentage scale (example values: 100% action=all plants dead or not emerged; 50% action=50% of the plants and green plant parts dead or not emerged; 0% action=no discernible action=like control plot). The score figures of in any case 2 repetitions (pots) were averaged.

When applying the combinations according to the invention, herbicidal effects are frequently observed on a harmful plant species which exceed the formal total of the effects of the herbicides present when these are applied by themselves.

Alternatively, it is observed in some cases that a lower application rate is required for the herbicide combination in order to achieve the same effect on a harmful plant species in comparison with the individual products. Such increases in action or efficacy, or reduced application rates, strongly suggest a synergistic effect.

When the data observed already exceed the formal total of the data in the experiments with individual applications, they likewise exceed the expected value according to Colby, which is calculated using the formula below and is likewise regarded as an indication of synergism (cf. S. R. Colby; in Weeds 15 (1967) pp. 20 to 22):

$$E=A+B-(A\cdot B/100)$$

In this formula:

A=action of active compound (A) in % at an application rate of a g of AS/ha;

B=action of active compound (B) in % at an application rate of b g of AS/ha;

E=expected value of the action of the combination (A)+(B) in % at the combined application rate a+b g of AS/ha.

The data observed in the experiments show, at suitably low dosages, an action of the combinations which exceeds the expected values according to Colby.

2. Post-emergence Herbicidal Action

Seeds or rhizome pieces of monocotyledonous and dicotyledonous weeds are placed in sandy loam in pots, covered with soil and grown in the greenhouse under good growth conditions (temperature, atmospheric humidity, water supply). Three weeks after sowing, the test plants are treated in the three-leaf stage with the compositions according to the invention. The compositions according to the invention, formulated as wettable powders or emulsion concentrates, are sprayed onto the green plant parts in various dosages using an application rate of 300 to 800 l of water/ha (converted). After the test plants have remained in the greenhouse under optimum growth conditions for about 3 to 4 weeks, the effect of the preparations is scored visually in comparison with untreated controls (scoring as in Example 1). The compositions according to the invention also have good herbicidal post-emergence action against a broad spectrum of economically important weed grasses and broad-leaf weeds.

Here, effects of the combinations according to the invention are frequently observed which exceed the formal total of the effects of the herbicides when these are applied by themselves. The observed values for the tests show, at suitably low dosages, an effect of the combinations which exceeds the expected values according to Colby (cf. scoring in Example 1).

3. Pre- and Post-emergence Herbicidal Action (Outdoor Trials)

Corresponding to the greenhouse experiments of sections 1 and 2, the tests were carried out in the open on plots. Scoring was carried out analogously to the tests in sections 1 and 2.

4. Herbicidal Action and Crop Plant Tolerance (Outdoor Trials)

Crop plants were grown in the open on plots under natural outdoor conditions, and seeds or rhizome pieces of typical harmful plants were laid out or the natural weed growth was utilized. Treatment with the compositions according to the invention was carried out after the harmful plants had emerged and the crop plants were, generally, at the 2- to 4-leaf stage; in some cases (as stated), application of individual active compounds or active compound combinations was carried out pre-emergence or as a sequential treatment partly pre-emergence and/or post-emergence.

In the case of plantation crops, it was generally only the soil between the individual crop plants that was treated with the active compounds.

After the application, for example 2, 4, 6 and 8 weeks after application, the effect of the preparations was scored visually by comparison with untreated controls (cf. scoring in Example 1). In the outdoor trial as well, the compositions according to the invention have synergistic herbicidal activity against a broad spectrum of economically important weed grasses and broad-leaf weeds. The comparison showed that the combinations according to the invention in most cases have a higher, in some cases a considerably higher, herbicidal activity than the total of the activities of the individual herbicides, thus indicating synergism. Moreover, the effects in essential phases of the scoring period were above the expected values according to Colby (cf. scoring in Example 1), also indicating synergism. In contrast, the crop plants were, as a consequence of the treatments with the herbicidal compositions, damaged only to a small degree, if at all.

5. Specific Test Examples

The following abbreviations are used in the description and the tables below:

g of AS/ha=grams of active substance (=100% active compound) per hectare;

the total of the activities of the individual applications is given as $E^A$;

the expected values according to Colby are in each case given as $E^C$;

Example 5.1

Certain combinations were tested for their herbicidal activity in accordance with the general example 1 (pre-emergence method). The results are summarized in Table 4.

TABLE 4

| Active compound(s) | Application rate [g of AS/ha] | Herbicidal action [%] against *Ipomoea hederifolia* |
|---|---|---|
| (A21) | 0.5 | 45 |
| | 0.2 | 0 |
| (B1.1.2) | 2.0 | 50 |
| | 0.5 | 5 |
| (A21) + (B1.1.2) | 0.2 + 0.5 | 67 |
| | | ($E^A$ = 0 + 5, $E^C$ = 0 + 5) |

Abbreviations and conditions in Table 4:

Conditions: pot trials/greenhouse, application by the pre-emergence method, evaluation 27 days after treatment AS = active substance (based on 100% of active compound)

(A21) = compound (A21) from Table 1 = 2-amino-4-[(1R,2S)-2,6-dimethyl-indan-1-ylamino]-6-[(1R)-1-fluoroethyl]-1,3,5-triazine (B1.1.2) = thiencarbazone-methyl = methyl 4-[(4,5-dihydro-3-methoxy-4-methyl-5-oxo-1H-1,2,4-triazol-1-yl)carbonylsulfamoyl]-5-methylthiophene-3-carboxylate Example 5.2

Certain combinations were tested for their herbicidal activity in accordance with the general example 1 (pre-emergence method). The results are summarized in Table 5.

TABLE 5

| Active compound(s) | Application rate [g of AS/ha] | Herbicidal action [%] against *Erodium cicutarium* |
|---|---|---|
| (A21) | 0.8 | 25 |
| | 0.2 | 0 |
| (B1.2.1) | 50 | 30 |
| (A21) + (B1.2.1) | 0.2 + 50 | 75 |
| | | ($E^A$ = 0 + 30, $E^C$ = 0 + 30) |
| (B1.3) | 15 | 65 |
| (A21) + (B1.3) | 0.2 + 15 | 75 |
| | | ($E^A$ = 0 + 65, $E^C$ = 0 + 65) |

TABLE 5-continued

| Active compound(s) | Application rate [g of AS/ha] | Herbicidal action [%] against *Erodium cicutarium* |
|---|---|---|
| (B1.4.1) | 5 | 50 |
| (A21) + (B1.4.1) | 0.2 + 5 | 68 |
| | | ($E^A$ = 0 + 50, $E^C$ = 0 + 50) |
| (B1.6.1) | 30 | 55 |
| (A21) + (B1.6.1) | 0.2 + 30 | 75 |
| | | ($E^A$ = 0 + 55, $E^C$ = 0 + 55) |

Abbreviations and conditions in Table 5: Conditions: in each case pot trials/greenhouse, application by the pre-emergence method, evaluation 28 days after treatment AS = active substance (based on 100% active compound)(A21) = compound (A21) from Table 1 = 2-amino-4-[(1R,2S)-2,6-dimethyl-indan-1-ylamino]-6-[(1R)-1-fluoroethyl]-1,3,5-triazine (B1.2.1) = tembotrione = 2-{2-chloro-4-mesyl-3-[(2,2,2-trifluoroethoxy)methyl]-benzoyl}cyclohexane-1,3-dione (B1.3) = ethyl [[3-[2-chloro-5-[3,6 dihydro-3-methyl-2,6-dioxo-4-(trifluoromethyl)-1-(2H)-pyrimidinyl]-4-fluorophenoxy]-2-pyridinyl]oxy]acetate (B1.4.1) = N-(5,7-dimethoxy[1,2,4]triazolo[1,5-a]pyrimidin-2-yl)-2-methoxy-4-(trifluoromethyl)pyridine-3-sulfonamide (B1.6.1) = 4-hydroxy-3-[[2-[(2-methoxyethoxy)methyl]-6-trifluoromethyl-3-pyridinyl]carbonyl]bicyclo[3.2.1]oct-3-en-2-one Example 5.3

Certain combinations were tested for their herbicidal activity in accordance with the general example 1 (pre-emergence method). The results are summarized in Table 6.

TABLE 6

| Active compound(s) | Application rate [g of AS/ha] | Herbicidal action [%] against *Geranium dissectum* |
|---|---|---|
| (A21) | 1.2 | 20 |
| | 0.3 | 5 |
| (B2.1.1) | 30 | 20 |
| (A21) + (B2.1.1) | 0.3 + 30 | 65 |
| | | ($EA^A$ = 5 + 20, $E^C$ = 24) |
| (B2.2.2) | 25 | 45 |
| (A21) + (B2.2.2) | 0.3 + 25 | 60 |
| | | ($E^A$ = 5 + 45, $E^C$ = 47.8) |
| (B2.3.1) | 50 | 65 |
| (A21) + (B2.3.1) | 0.3 + 50 | 80 |
| | | ($E^A$ 5 + 65, $E^C$ = 66.8) |
| (B2.4.1) | 75 | 50 |
| (A21) + (B2.4.1) | 0.3 + 75 | 85 |
| | | ($E^A$ = 5 + 50, $E^C$ = 52.5) |
| (B2.5) | 300 | 35 |
| (A21) + (B2.5) | 0.3 + 300 | 55 |
| | | ($E^A$ = 5 + 35, $E^C$ = 38.3) |
| (B2.6.1) | 100 | 65 |
| (A21) + (B2.6.1) | 0.3 + 100 | 95 |
| | | ($E^A$ = 5 + 65, $E^C$ = 66.8) |
| (B3.1) | 50 | 50 |
| (A21) + (B3.1) | 0.3 + 50 | 75 |
| | | ($E^A$ = 5 + 50, $E^C$ = 52.5) |

Abbreviations and conditions in Table 6:

Conditions: in each case pot trial/greenhouse, application by the pre-emergence method, evaluation 28 days after treatment AS = active substance (based on 100% active compound)

(A21) = compound (A21) from Table 1 = 2-amino-4-[(1R,2S)-2, 6-dimethyl-indan-1-ylamino]6-[(1R)-1-fluoroethyl]-1,3,5-triazine (B2.1.1) = pyrasulfotole = (5-hydroxy-1,3-dimethyl-1H-pyrazol-4-yl)-[2-(methylsulfonyl)-4-(trifluoromethyl)phenyl]methanone (B2.2.2) = trifloxysulfuron sodium salt = 1-(4,6-dimethoxypyrimidin-2-yl)-3-[3-(2,2,2-trifluoroethoxy)-2-pyridylsulfonyl]urea sodium salt (B2.3.1) = saflufenacil = 2-chloro-5-[3,6-dihydro-3-methyl-2,6-dioxo-4-(trifluoromethyl)-1(2H)-pyrimidinyl]-4-fluoro-N-[[methyl(1-methylethyl)amino]sulfonyl]benzamide (B2.4.1) = aminopyralid = 4-amino-3,6-dichloropyridine-2-carboxylic acid (B2.5) = ethofumesate = (RS)—O-(2-ethoxy-2,3-dihydro-3,3-dimethylbenzofuran-5-yl) methanesulfonate (B2.6.1) = aminocyclopyrachlor = 6-amino-5-chloro-2-cyclopropylpyrimidine-4-carboxylic acid (B3.1) = pyroxasulfone = 3-[5-(difluoromethoxy)-1-methyl-3-(trifluoromethyl)-pyrazol-4-ylmethylsulfonyl]-4,5-dihydro-5,5-dimethyl-1,2-oxazole

The invention claimed is:

[1. A herbicide combination comprising:

an effective amount of components (A) and (B);

wherein component A includes one or more herbicidally active compounds (A) selected from the group consisting of:

(A21)

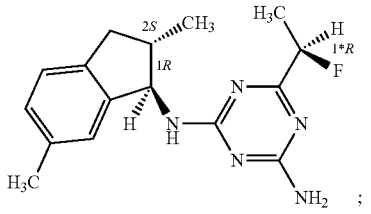

wherein component (B) is one or more herbicidally active compounds (B) selected from the group consisting of:

(B1.2.1) tembotrione;

(B1.3) ethyl [[3-[2-chloro-5-[3,6-dihydro-3-methyl-2,6-dioxo-4-(trifluoromethyl)-1(2H)-pyrimidinyl]-4-fluorophenoxyl-2-pyridinyl]oxy]acetate (SYN-523);

(B1.4.1) pyroxsulam;

(B1.6.1) 4-hydroxy-3-[[2-[(2-methoxyethoxy)methyl]-6-trifluoromethyl-3-pyridinyl]carbonyl]bicyclo[3.2.1] oct-3-en-2-one (SYN-449);

(B2.2.2) trifloxysulfuron sodium salt;

(B2.3.1) saflufenacil;

(B2.4.1) aminopyralid;

(B2.5) ethofumesate; and (B3.1) pyroxasulfone (KIH-485).]

[2. The herbicide combination as claimed in claim 1; wherein active compound components (A) and (B) are present in a weight ratio of from 1:100000 to 2000:1.]

[3. The herbicide combination as claimed in claim 1; wherein active compound components (A) and (B) are present in a weight ratio of from 1:40000 to 750:1.]

[4. The herbicide combination as claimed in claim 1; which comprises one or more further components from the group comprising crop protection agents.]

[5. A herbicidal composition which comprises:

the herbicide combination as claimed in claim 1; and one or more additives customary in crop protection.]

[6. A method for controlling harmful plants which comprises:

applying a synergistically effective amount of the active compound components of the herbicide combination as defined in claim 1 together or separately, by the pre-emergence method, by the post-emergence method, or by the pre-emergence and the post-emergence method, onto the plants, parts of plants, plant seeds, or the area where the plants grow.]

[7. The method as claimed in claim 6; wherein the herbicide component (A) is applied in an application amount of from 0.01 to 2000 g of active substance per hectare and the herbicide component (B) is applied in an application amount of from 0.01 to 1000 g of active substance per hectare.]

[8. The method as claimed in claim 6 for the control of harmful plants on non-crop land or in plantation crops.]

[9. The method as claimed in claim 6; wherein the active compounds of the herbicide combination are applied in the form of a herbicidal composition which comprises one or more additives customary in crop protection, if appropriate after dilution with water.]

*10. A herbicide combination comprising:*

*a synergistically effective amount of components (A) and (B);*

*wherein component A comprises:*

(A21)

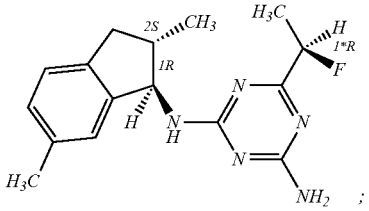

*wherein component (B) comprises one or more compounds (B) selected from the group consisting of:*

*(B2.6) aminocyclopyrachlor and its salts and esters.*

*11. The herbicide combination as claimed in claim 10; wherein components (A) and (B) are present in a weight ratio of from 1:100000 to 2000:1.*

*12. The herbicide combination as claimed in claim 10; wherein components (A) and (B) are present in a weight ratio of from 1:40000 to 750:1.*

*13. The herbicide combination as claimed in claim 10; wherein components (A) and (B) are present in a weight ratio of from 1:75000 to 200:1.*

*14. The herbicide combination as claimed in claim 10; components (A) and (B) are present in a weight ratio of from 1:25000 to 75:1.*

*15. The herbicide combination as claimed in claim 10; which comprises one or more crop protection agents.*

*16. A herbicidal composition which comprises:*

*the herbicide combination as claimed in claim 10; and one or more additives customary in crop protection.*

*17. A method of controlling harmful plants, said method comprising applying an herbicide combination according to claim 10 together or separately, by the pre-emergence method, by the post-emergence method, or by the pre-emergence and the post-emergence method, onto the plants, parts of plants, plant seeds, or the area where the plants grow on a path, rail track, or industrial terrain.*

*18. The method as claimed in claim 17; wherein the herbicide component (A) is applied in an application amount of from 0.01 to 2000 g of active substance per hectare and the herbicide component (B) is applied in an application amount of from 0.01 to 1000 g of active substance per hectare.*

*19. The method as claimed in claim 17; wherein component (B) is applied in an application amount of from 2 to 350 g of active substance per hectare.*

*20. The method as claimed in claim 17; wherein the active compounds of the herbicide combination are applied in the form of a herbicidal composition which comprises one or more additives customary in crop protection, if appropriate after dilution with water.*

*21. A method of reducing plant damage, said method comprising applying an herbicide combination according to claim 10 to a plant, part of a plant, plant seed, and/or the area where the plant grows.*

*22. The herbicide combination as claimed in claim 10; wherein component (B) comprises one or more herbicidally active compounds (B) selected from the group consisting of (B2.6) aminocyclopyrachlor and its salts.*

*23. The herbicide combination as claimed in claim 10; wherein component (B) comprises one or more herbicidally active compounds (B) selected from the group consisting of (B2.6) aminocyclopyrachlor and its esters.*

*24. The herbicide combination as claimed in claim 10; wherein component (B) comprises (B2.6.1) aminocyclopyrachlor.*

*25. The herbicide combination as claimed in claim 10, further comprising imazapyr.*

* * * * *